(12) United States Patent
Ketchem et al.

(10) Patent No.: US 11,384,140 B2
(45) Date of Patent: Jul. 12, 2022

(54) DIRECT SELECTION OF CELLS EXPRESSING HIGH LEVELS OF HETEROMERIC PROTEINS USING GLUTAMINE SYNTHETASE INTRAGENIC COMPLEMENTATION VECTORS

(71) Applicant: AMGEN INC., Thousand Oaks, CA (US)

(72) Inventors: Randal Robert Ketchem, Snohomish, WA (US); Jeffrey T. McGrew, Woodinville, WA (US); Dina A. Fomina Yadlin, Kirkland, WA (US)

(73) Assignee: Amgen Inc., Thousand Oaks, CA (US)

( * ) Notice: Subject to any disclaimer, the term of this patent is extended or adjusted under 35 U.S.C. 154(b) by 668 days.

(21) Appl. No.: 16/099,986

(22) PCT Filed: May 11, 2017

(86) PCT No.: PCT/US2017/032139
§ 371 (c)(1),
(2) Date: Nov. 8, 2018

(87) PCT Pub. No.: WO2017/197098
PCT Pub. Date: Nov. 16, 2017

(65) Prior Publication Data
US 2019/0127452 A1     May 2, 2019

Related U.S. Application Data

(60) Provisional application No. 62/334,966, filed on May 11, 2016.

(51) Int. Cl.
| | |
|---|---|
| *C12N 15/65* | (2006.01) |
| *C12N 15/67* | (2006.01) |
| *C07K 16/18* | (2006.01) |
| *C07K 16/06* | (2006.01) |
| *C12N 15/85* | (2006.01) |

(52) U.S. Cl.
CPC ............ *C07K 16/18* (2013.01); *C07K 16/065* (2013.01); *C12N 15/65* (2013.01); *C12N 15/67* (2013.01); *C12N 15/85* (2013.01); *C07K 2319/30* (2013.01); *C12N 2015/8518* (2013.01); *C12Y 603/01002* (2013.01)

(58) Field of Classification Search
CPC ..... C07K 16/18; C07K 2317/00; C12N 15/65
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,225,539 A | 7/1993 | Winter | |
| 5,573,925 A | 11/1996 | Halazonetis | |
| 5,624,818 A | 4/1997 | Eisenman et al. | |
| 5,877,293 A | 3/1999 | Adair et al. | |
| 5,886,152 A | 3/1999 | Nakatani et al. | |
| 5,916,771 A | 6/1999 | Hori et al. | |
| 6,054,297 A | 4/2000 | Carter et al. | |
| 6,696,245 B2 | 2/2004 | Winter et al. | |
| 6,846,634 B1 | 1/2005 | Tomlinson et al. | |
| 7,442,778 B2 | 10/2008 | Gegg et al. | |
| 7,691,605 B2 * | 4/2010 | McGrew ................ | C12N 15/62 435/69.1 |
| 8,053,238 B2 | 11/2011 | Jin et al. | |
| 2003/0039958 A1 | 2/2003 | Holt et al. | |
| 2003/0082735 A1 | 5/2003 | McGrew et al. | |
| 2004/0009507 A1 | 1/2004 | Winter et al. | |
| 2004/0038291 A2 | 2/2004 | Tomlinson et al. | |
| 2004/0202995 A1 | 10/2004 | de Wildt et al. | |
| 2005/0202512 A1 | 9/2005 | Tomlinson et al. | |
| 2007/0254338 A1 | 11/2007 | Caspary et al. | |
| 2013/0244231 A1 | 9/2013 | Takahashi | |

FOREIGN PATENT DOCUMENTS

| | | |
|---|---|---|
| CN | 1966682 A | 5/2007 |
| EP | 0125023 B1 | 6/1991 |
| EP | 0519596 B1 | 5/1992 |
| EP | 0120694 B1 | 7/1993 |
| EP | 0194276 B1 | 8/1993 |
| EP | 0239400 B1 | 8/1994 |
| EP | 0451216 B1 | 1/1996 |
| WO | 1989/001533 A1 | 2/1989 |
| WO | 1993/008207 A1 | 4/1993 |
| WO | 1996/040918 A2 | 12/1996 |
| WO | 1998/044350 A1 | 10/1998 |
| WO | 2005/024015 A1 | 3/2005 |
| WO | 2008/154014 A3 | 12/2008 |

(Continued)

OTHER PUBLICATIONS

Alberti et al., Genetic Analysis of the Leucine Heptad Repeats of Lac Repressor: Evidence for a 4-Helical Bundle, Embo Journal (1993), 12(8):3227-3236.

Aldrich et al., EASE Vectors for Rapid Stable Expression of Recombinant Antibodies, Biotechnol. Prog. (2003), 19:1443-1438.

Bird et al., Single-Chain Antigen-Binding Proteins, Science (1988), 242:423-426.

Catapano et al., Bioreactor Design and Scale-Up, Cell and Tissue Reaction Engineering: Principles and Practice (2009), Chapter 5:173-259.

Chakerian et al., Evidence for Leucine Zipper Motif in Lactose Repressor Protein, J. Biol. Chem. (1991), 266(3): 1371-1374.

Chaudhary et al., A Recombinant Immunotoxin Consisting of Two Antibody Variable Domains Fused to *Pseudomonas* Exotoxin, Nature (1989), 339:394-397.

(Continued)

*Primary Examiner* — Maryam Monshipouri
(74) *Attorney, Agent, or Firm* — Henry P. Wu

(57) ABSTRACT

This invention relates to the general field of recombinant expression of polypeptides in animal cell culture. More specifically, the invention concerns improved selection of cells transfected with recombinantly engineered vectors designed to express polypeptides, in particular heteromultimeric polypeptides.

21 Claims, 6 Drawing Sheets

Specification includes a Sequence Listing.

(56) References Cited

FOREIGN PATENT DOCUMENTS

WO        2012/095514 A1     7/2012

OTHER PUBLICATIONS

Chothia et al., Canonical Structures for the Hypervariable Regions of Immunoglobulins, J. Mol. Biol. (1987), 196:901-917.
Chothia et al., Confirmations of Immunoglobulin Hypervariable Regions, Nature (1989), 342:877-883.
Clore et al., High-Resolution Structure of the Oligomerization Domain of p53 by Multidimensional NMR, Science (1994), 265:386.
Colberre-Garapin et al., A New Dominant Hybrid Selective Marker for Higher Eukaryotic Cells, J. Mol. Biol. (1981), 150(1):1-14.
Curtis et al., Enhanced Hematopoietic Activity of a Human Granulocyte/Macrophage Colony-Stimulating Factor-Interleukin 3 Fusion Protein, Proc. Natl. Acad. Sci. (1991), 88(13):5809-5813.
Davies and Kaufman, The Sequence Context of the Initiation Codon in the Encephalomyocarditis Virus Leader Modulates Efficiency of Internal Translation Initiation, J. Virology (1992), 66(4):1924-1932.
Harbury et al., A Switch Between Two-, Three-, and Four-Stranded Coiled Coils in GCN4 Leucine Zipper Mutants, Science (1993), 262:1401-1407.
Holliger et al., "Diabodies": Small Bivalent and Bispecific Antibody Fragments, Proc. Natl. Acad. Sci. USA (1993), 90:6444-6448.
Honegger et al., Yet Another Numbering Scheme for Immunoglobulin Variable Domains: An Automatic Modeling and Analysis Tool, J. Mol. Biol. (2001), 309:657-670.
Huston et al., Protein Engineering of Antibody Binding Sites: Recovery of Specific Activity in an Anti-Digoxin Single-Chain Fv Analogue Produced in *Escherichia coli*, Proc. Natl. Acad. Sci. USA (1988), 85:5879-5883.
Jang et al., Cap-Independent Translation of Encephalomyocarditis Virus RNA: Structural Elements of the Internal Ribosomal Entry Site and Involvement of a Cellular 57-kD RNA-Binding Protein, Genes & Development (1990), 4(9):1560-1572.
Jang et al., Initiation of Protein Synthesis by Internal Entry of Ribosomes into the 5' Nontranslated Region of Encephalomyocarditis Virus RNA In Vivo, J. Virology (1989), 63(4):1651-1660.
Korndorfer et al., Crystallographic Analysis of an "Anticalin" with Tailored Specificity for Fluorescein Reveals High Structural Plasticity of the Lipocalin Loop Region, Proteins: Structure, Function, and Bioinformatics (2003), 53:121-129.
Kurokawa et al., Differential Orientations of the DNA-Binding Domain and Carboxy-Terminal Dimerization Interface Regulate Binding Site Selection by Nuclear Receptor Heterodimers, Genes Dev (1993), 7:1423-1435.
Kuystermans et al., Bioreactor Systems for Producing Antibody from Mammalian Cells, Antibody Expression and Production, Cell Engineering (2011), 9:25-52.
Larrick et al., Polymerase Chain Reaction Using Mixed Primers: Cloning of Human Monoclonal Antibody Variable Region Genes from Single Hybridoma Cells, Biotechnology (1989), 7(9):934-938.
Lewis et al., Crystal Structure of the Lactose Operon Repressor and its Complexes with DNA and Inducer, Nature (1996), 271:1247.
Lowy et al., Isolation of Transforming DNA: Cloning the Hamster aprt Gene, Cell (1980), 22:817-823.
MacNeil et al., Fine Structure Deletion Map and Complementation Analysis of the GLN-A-GLN-L-GLN-G Region in *Escherichia-coli*, J. of Bateriology (1982) 150(3):1302-1313.
Marmonstein et al., DNA Recognition by GAL4: Structure of a Protein-DNA Complex, Nature (1992), 356:408-414.
Milstein et al., Hybrid Hybridomas and Their Use in Immunohistochemistry, Nature (1983), 305:537-540.
Mitchell, The GLN-1 Locus of *Saccharomyces-cerevisiae* Encodes Glutamine Synthetase, Genetics (1985), 111(2):243-258.
Mulligan et al., Selection for Animal Cells that Express the *Escherichia coli* Gene Coding for Xanthine-Guanine Phosphoribosyl Transferase, Proc. Natl. Acad. Sci.. (1981), 78:2072.
Murre et al., Interactions Between Heterologous Helix-Loop-Helix Proteins Generate Complexes that Bind Specifically to a Common DNA Sequence, Cell (1989), 58(3):537-544.
Pelletier et al., Oligomerization Domain-Directed Reassembly of Active Dihydrofolate Reductase from Rationally Designed Fragments, Proc. Natl. Acad. Sci. USA (1998), 95:12141-12146.
Poljak et al., Production and Structure of Diabodies, Structure (1994), 2:1121-1123.
Rasmussen et al., Isolation, Characterization and Recombinant Protein Expression in Veggie-CHO: A Serum-Free CHO Host Cell Line, Cytotechnology (1998), 28:31-42.
Reichmann et al., Reshaping Human Antibodies for Therapy, Nature (1988), 332:323-327.
Remy and Michnick, Clonal Selection and In Vivo Quantitation of Protein Interactions with Protein-Fragment Complementation Assays, Proc. Natl. Acad. Sci. (1999), 96:5394-5399.
Remy and Michnick, Visualization of Biochemical Networks in Living Cells, Proc. Natl. Acad. Sci. (2001), 98:7678-7683.
Roberts et al., Generation of an Antibody with Enhanced Affinity and Specficity for its Antigen by Proteins Engineering, Nature (1987), 328:731-734.
Rodriguez-Pombo et al., Towards a Model to Explain the Intragenic Complementation in the Heteromultimeric Protein Propionyl-CoA Carboxylase. Biochimica et Biophysica Acta. Molecular Basis of Disease (2005), 1740(3):489-498.
Roque et al., Antibodies and Genetically Engineered Related Molecules: Production and Purification, Biotechnol. Prog. (2004), 20:639-654.
Santerre et al., Expression of Prokaryotic Genes for Hygromycin B and G418 Resistance as Dominant-Selection Markers in Mouse L Cells, Gene (1984), 30(1-3):147-156.
Stettler et al., New Disposable Tubes for Rapid and Precise Biomass Assessment for Suspension Cultures of Mammalian Cells, Biotechnol, Bioeng, (2006), 95(6):1228-1233.
Szybalska & Szybalski, Genetics of Human Cell Line. OV. DINA-Mediated Heritable Transformation of a Biochemical Trait, Proc. Natl. Acad. Sci. USA (1962), 48:2026-2034.
Trevisson et al., Functional Complementation in Yeast Allows Molecular Characterization of Missense Argininosuccinate Lyase Mutations, J. of Biol, Chem. (2009), 284(42):28926-28934.
Verhoeyen et al., Reshaping of Human Antibodies: Grafting an Antilysozyme Activity, Science (1988), 239:1534-1536.
Voisard et al., Potential of Cell Retention Techniques for Large-Scale High-Density Perfusion Culture of Suspended Mammalian Cells, Biotechnol. Bioeng. (2003), 82:751-765.
Walker et al., Intragenic Complementation at the Human Argininosuccinate Lyase Locus. Identification of the Major Complementing Alleles, J. of Biol, Chem, (1997), 272(10):6777-6783.
Ward et al., Binding Activities of a Repertoire of Single Immunoglobulin Variable Domains Secreted from *Escherichia coli*, Nature (1989), 341:544-546.
Wigler et al., Transfer of Purified Herpes Virus Thymidine Kinase Gene to Cultured Mouse Cells, Cell (1977), 11(1):223-232.
Ye et al., Rapid Protein Production Using CHO Stable Transfection Pools, Biotechnol. Prog, (2010), 26(5):1431-1437.
Yu et al., Mechanisms for Intragenic Complementation at the Human Arginonosuccinate Lyase Locus, Biochem, (2001), 40(51):15581-15590.
Zhang et al., Antibody-Promoted Dimerization Bypasses the Regulation of DNA Binding by the Heme Domain of the Yeast Transcriptional Activator HAP1, Proc. Natl. Acad. Sci. USA (1993) 90:2851-2855.
Bianchi, A. A. and McGrew, J. T., High-Level Expression of Full-Length Antibodies Using Trans-Complementing Expression Vectors. Biotechnology and Bioengineering, Nov. 20, 2003, vol. 84, No. 4, pp. 439-444 p. 440, 441, 443, Fig 1 & 5.
Fan, L. et al., The use of glutamine synthetase as a selection marker: recent advances in Chinese hamster ovary cell generation processes, *Pharmaceutical Bioprocessing*, Dec. 2013, vol. 1, No. 5, pp. 487-502.

(56) References Cited

OTHER PUBLICATIONS

Shaimardanova, A.A. et al., Production and Application of Multicistronic Constructs for Various Disease Therapies, Pharmaceutics Nov. 6, 2019, vol. 11, p. 580.

* cited by examiner

DIRECT SELECTION OF CELLS EXPRESSING HIGH LEVELS OF HETEROMERIC PROTEINS USING GLUTAMINE SYNTHETASE INTRAGENIC COMPLEMENTATION VECTORS

CROSS-REFERENCE TO RELATED APPLICATIONS

This application claims the benefit of U.S. Provisional Application No. 62/334,966 filed May 11, 2016, which is hereby incorporated by reference in its entirety.

DESCRIPTION OF THE TEXT FILE SUBMITTED ELECTRONICALLY

The present application contains a Sequence Listing, which has been submitted electronically in ASCII format and is hereby incorporated by reference in its entirety. The computer readable format copy of the Sequence Listing, which was created on May 8, 2017, is named A-2011-WO-PCT_SEQ_ST25.txt and is 79.1 kilobytes in size.

FIELD OF THE INVENTION

This invention relates to the general field of recombinant expression of polypeptides in mammalian cell culture. More particularly, the invention concerns improved selection in cells of recombinantly engineered vectors designed to express heteromeric polypeptides.

BACKGROUND OF THE INVENTION

Expression of heteromeric recombinant proteins usually requires similar expression of component chains in order to avoid unnecessary synthesis of chains that cannot be incorporated into mature proteins. Additionally, most methods for producing heteromeric recombinant proteins require screening of many clones in order to identify rare high expressing clones that express high levels of each chain of the mature heteromeric protein. A split selectable marker system (in which a selectable marker is split into two pieces and each fragment is linked to expression of one chain of the heteromeric protein can be used to identify those cells that express both selectable marker fragments and hence, both chains of the heteromeric proteins.

Glutamine synthetase (GS) catalyzes glutamine biosynthesis by the condensation of ammonia with glutamate Mammalian GS enzyme is a decamer composed of two stacked pentameric rings, with ten active sites located at the junction of subunits. Each active site is formed by residues from the N-terminal domain (the β-grasp domain, composed of residues 25-112) of one subunit and by residues from the C-terminal domain (the catalytic domain, composed of residues 113-373) of an adjacent subunit. Genetic studies in *S. cerevisiae* and *E. coli* showed that certain GS mutations displayed intragenic complementation, where some mutations that mapped to the 5' end of the GS gene could complement those in the 3' end (Mitchell, A. P. *Genetics* 111, 243-258 (1985); MacNeil, T., et al. *Journal of Bacteriology* 150, 1302-1313 (1982)). Accordingly, identifying a selection system based on a metabolic enzyme, such as one that utilizes intragenic complementation of glutamine synthetase, would prove useful for expressing molecules with more than two unique polypeptide chains (e.g. monoclonal antibodies and other recombinant proteins).

SUMMARY OF THE INVENTION

One embodiment of the invention provides a vector comprising:
a. a first nucleic acid encoding a first polypeptide, and
b. a second nucleic acid encoding a second polypeptide, wherein the second polypeptide is an initial mutant subunit of a selectable marker,
   wherein the transcription of the first nucleic acid is operably linked to transcription of the second nucleic acid, further comprising:
c. a third nucleic acid encoding a third polypeptide wherein the third polypeptide is capable of associating with the first polypeptide to form a heteromeric complex, and
d. a fourth nucleic acid which encodes fourth polypeptide, wherein the fourth polypeptide is a complementary mutant subunit of the selectable marker,
   wherein the transcription of the third nucleic acid is operably linked to transcription of the fourth nucleic acid,
wherein the initial mutant subunit and the complementary mutant subunit of the selectable marker interact to provide a selectable activity, and further wherein the vector is capable of being transfected into mammalian cells and improving selection of transfected cells.

Another embodiment of the invention provides a vector comprising:
e. a first nucleic acid encoding a first polypeptide, and
f. a second nucleic acid encoding a second polypeptide, wherein the second polypeptide is an initial fragment of a selectable marker,
   wherein the transcription of the first nucleic acid is operably linked to transcription of the second nucleic acid, further comprising:
g. a third nucleic acid encoding a third polypeptide wherein the third polypeptide is capable of associating with the first polypeptide to form a heteromeric complex, and
h. a fourth nucleic acid which encodes fourth polypeptide, wherein the fourth polypeptide is a complementary fragment of the selectable marker,
   wherein the transcription of the third nucleic acid is operably linked to transcription of the fourth nucleic acid,
wherein the initial mutant subunit and the complementary mutant subunit of the selectable marker interact to provide a selectable activity, and further wherein the vector is capable of being transfected into mammalian cells and improving selection of transfected cells.

In a further embodiment, the heteromeric complex is an immunoglobulin. In one embodiment, the first nucleic acid encodes an immunoglobulin heavy chain, and the third nucleic acid encodes an immunoglobulin light chain, in an alternative embodiment, the first nucleic acid encodes an immunoglobulin light chain, and the third nucleic acid encodes an immunoglobulin heavy chain. In the aforementioned embodiments, the selectable marker is metabolic enzyme is selected from the group consisting of glutamine synthetase, threonine dehydratase, adenylosuccinate synthetase, and glutamate dehydrogenase.

The invention may include an internal ribosomal entry site (IRES); in one embodiment, an IRES occurs at a site selected from the group consisting of: a site between the first nucleic acid and the second nucleic acid; a site between the third nucleic acid and the fourth nucleic acid, and at sites between both first and second, and third and fourth nucleic acids. In a further embodiment, the internal ribosomal entry site comprises SEQ ID NO:23.

For any of the herein described embodiments, when the initial mutant subunit of the selectable marker is an N-terminal mutant of glutamine synthetase (mutGS-NT) the complementary mutant subunit of the selectable marker is a C-terminal mutant of glutamine synthetase (mutGS-CT).

In one such aspect of the invention, the mutGS-NT comprises two or more mutations selected from the group consisting of W60A N61A D63A D63R S66A and D76A and the mutGS-CT comprises one or more mutations selected from the group consisting of E134A E136A E196A E203A N248A H253A N255A R319A and R324A. In one embodiment, mutGS-NT is selected from the group consisting of W60A N61A D63A (mutGS-NT1; SEQ ID NO:6), W60A N61A D63A S66A (mutGS-NT2; SEQ ID NO:10) W60A N61A D63A S66A D76A (mutGS-NT3; SEQ ID NO:25), and W60A N61A D63R S66A (mutGS-NT4; SEQ ID NO:19); and the mutGS-CT is selected from the group consisting of E134A E136A E196A E203A (mutGS-CT1; SEQ ID NO:21) and N248A H253A N255A (mutGS-CT2; SEQ ID NO:22).

In other embodiments, N-terminal and C-terminal fragments of glutamine synthetase are created by splitting the protein at one or more amino acids of the glutamine synthetase protein. In one such aspect of the invention, the N-terminal fragment and/or C-terminal fragments of glutamine synthetase are split at an amino acid of glutamine synthetase selected from the group consisting of: E110, Y104, S125, N126, E264, T111, N105, N126, Q127, and N265

The invention also provides an isolated host cell that has been transfected, transformed or transduced with the vector as described above. The host cell may be selected from the group consisting of CHO, VERO, BHK, HeLa, Cos, MDCK, 293, 3T3, a myeloma cell line, and WI38 cells. One aspect of the invention provides a method of producing a heteromeric complex comprising the step of culturing such a host cell under conditions wherein the heteromeric complex is expressed by the host cell. In one embodiment, the heteromeric complex is an antibody. The inventive methods of claim may also comprise isolating the heteromeric complex.

One embodiment of the invention provides an expression system comprising:
a) a first vector encoding a bicistronic transcript comprising a first nucleic acid encoding a first polypeptide that is operably linked to a second nucleic acid encoding a second polypeptide, wherein the second polypeptide is an initial mutant subunit of a selectable marker, and
b) a second vector encoding a bicistronic transcript comprising a third nucleic acid encoding a third polypeptide that is operably linked to a fourth nucleic acid encoding a fourth polypeptide, wherein the fourth polypeptide is a complementary mutant subunit of the selectable marker that is capable of associating with the initial mutant subunit of the selectable marker to provide a selectable activity,
further wherein the third polypeptide is capable of associating with the first polypeptide to form a heteromeric complex;
and further wherein the expression system is capable of being transfected into mammalian cells and improving selection of said cells.

Another embodiment of the invention provides an expression system comprising:
c) a first vector encoding a bicistronic transcript comprising a first nucleic acid encoding a first polypeptide that is operably linked to a second nucleic acid encoding a second polypeptide, wherein the second polypeptide is an initial fragment of a selectable marker, and
d) a second vector encoding a bicistronic transcript comprising a third nucleic acid encoding a third polypeptide that is operably linked to a fourth nucleic acid encoding a fourth polypeptide, wherein the fourth polypeptide is a complementary fragment of the selectable marker that is capable of associating with the initial fragment of the selectable marker to provide a selectable activity, further wherein the third polypeptide is capable of associating with the first polypeptide to form a heteromeric complex;
and further wherein the expression system is capable of being transfected into mammalian cells and improving selection of said cells.

In a further embodiment, the heteromeric complex is an immunoglobulin. In one embodiment, the first nucleic acid encodes an immunoglobulin heavy chain, and the third nucleic acid encodes an immunoglobulin light chain, in an alternative embodiment, the first nucleic acid encodes an immunoglobulin light chain, and the third nucleic acid encodes an immunoglobulin heavy chain. In the aforementioned embodiments, the selectable marker is metabolic enzyme is selected from the group consisting of glutamine synthetase, threoninedehydratase, adenylosuccinate synthetase, and glutamate dehydrogenase.

The inventive expression system described above may include an internal ribosomal entry site (IRES); in one embodiment, an IRES occurs at a site selected from the group consisting of: a site between the first nucleic acid and the second nucleic acid; a site between the third nucleic acid and the fourth nucleic acid, and at sites between both first and second, and third and fourth nucleic acids. In a further embodiment, the internal ribosomal entry site comprises SEQ ID NO:23.

In the herein described expression system, when the initial mutant subunit of the selectable marker is an N-terminal mutant of glutamine synthetase (mutGS-NT) the complementary mutant subunit of the selectable marker is a C-terminal mutant of glutamine synthetase (mutGS-CT). In one such aspect of the invention, the mutGS-NT comprises two or more mutations selected from the group consisting of W60A N61A D63A D63R S66A and D76A and the mutGS-CT comprises one or more mutations selected from the group consisting of E134A E136A E196A E203A N248A H253A N255A R319A and R324A. In one embodiment, mutGS-NT is selected from the group consisting of W60A N61A D63A (mutGS-NT1; SEQ ID NO:6), W60A N61A D63A S66A (mutGS-NT2; SEQ ID NO:10) W60A N61A D63A S66A D76A (mutGS-NT3; SEQ ID NO:25), and W60A N61A D63R S66A (mutGS-NT4; SEQ ID NO:19); and the mutGS-CT is selected from the group consisting of E134A E136A E196A E203A (mutGS-CT1; SEQ ID NO:21) and N248A H253A N255A (mutGS-CT2; SEQ ID NO:22).

In other embodiments, N-terminal and C-terminal fragments of glutamine synthetase are created by splitting the protein at one or more amino acids of the glutamine synthetase protein. In one such aspect of the invention, the N-terminal fragment and/or C-terminal fragments of glutamine synthetase are split at an amino acid of glutamine synthetase selected from the group consisting of: E110, Y104, S125, N126, E264, T111, N105, N126, Q127, and N265

The invention also provides an isolated host cell that has been transfected, transformed or transduced with the vector as described above. The host cell may be selected from the group consisting of CHO, VERO, BHK, HeLa, Cos, MDCK, 293, 3T3, a myeloma cell line, and WI38 cells. One aspect of the invention provides a method of producing a heteromeric complex comprising the step of culturing such a host cell under conditions wherein the heteromeric complex is expressed by the host cell. In one embodiment, the heteromeric complex is an antibody. The inventive methods of claim may also comprise isolating the heteromeric complex.

In one embodiment, the invention provides an expression system comprising a first vector comprising a first nucleic acid encoding a heavy chain of an antibody operably linked to a second nucleic acid that encodes an N-terminal mutant glutamine synthetase (mutGS-NT), and a second vector comprising a third nucleic acid encoding a light chain of an antibody operably linked a fourth nucleic acid that encodes a C-terminal mutant glutamine synthetase (mutGS-CT), wherein each mutant subunit of glutamine synthetase does not have selectable activity when expressed alone and co-expression of the mutGS-NT with the mutGS-CT provides glutamine synthetase activity, wherein the expression system is capable of being transfected into mammalian cells and improving selection of transfected cells.

In one embodiment, the invention provides an expression system comprising a first vector comprising a first nucleic acid encoding a heavy chain of an antibody operably linked to a second nucleic acid that encodes an N-terminal fragment of glutamine synthetase, and a second vector comprising a third nucleic acid encoding a light chain of an antibody operably linked a fourth nucleic acid that encodes a C-terminal fragment of glutamine synthetase, wherein each mutant subunit of glutamine synthetase does not have selectable activity when expressed alone and co-expression of the N-terminal and C-terminal fragments of glutamine synthetase provides glutamine synthetase activity, wherein the expression system is capable of being transfected into mammalian cells and improving selection of transfected cells.

In another embodiment, the invention provides an expression system comprising a first vector comprising a first nucleic acid encoding a light chain of an antibody operably linked to a second nucleic acid that encodes an N-terminal mutant glutamine synthetase (mutGS-NT), and a second vector comprising a third nucleic acid encoding a heavy chain of an antibody operably linked a fourth nucleic acid that encodes a C-terminal mutant glutamine synthetase (mutGS-CT), wherein each mutant subunit of glutamine synthetase does not have selectable activity when expressed alone and co-expression of the mutGS-NT with the mutGS-CT provides glutamine synthetase activity, wherein the expression system is capable of being transfected into mammalian cells and improving selection of transfected cells.

In another embodiment, the invention provides an expression system comprising a first vector comprising a first nucleic acid encoding a light chain of an antibody operably linked to a second nucleic acid that encodes an N-terminal fragment of glutamine synthetase, and a second vector comprising a third nucleic acid encoding a heavy chain of an antibody operably linked a fourth nucleic acid that encodes a C-terminal fragment of glutamine synthetase, wherein each fragment of glutamine synthetase does not have selectable activity when expressed alone and co-expression of the N-terminal and C-terminal fragments of glutamine synthetase provides glutamine synthetase activity, wherein the expression system is capable of being transfected into mammalian cells and improving selection of transfected cells.

For any of the forgoing embodiments, in one aspect of the invention the mutGS-NT comprises two or more mutations selected from the group consisting of W60A N61A D63A D63R S66A and D76A and the mutGS-CT comprises one or more mutations selected from the group consisting of E134A E136A E196A E203A N248A H253A N255A R319A and R324A. In one embodiment, mutGS-NT is selected from the group consisting of W60A N61A D63A (mutGS-NT1; SEQ ID NO:6), W60A N61A D63A S66A (mutGS-NT2; SEQ ID NO:10) W60A N61A D63A S66A D76A (mutGS-NT3; SEQ ID NO:25), and W60A N61A D63R S66A (mutGS-NT4; SEQ ID NO:19); and the mutGS-CT is selected from the group consisting of E134A E136A E196A E203A (mutGS-CT1; SEQ ID NO:21) and N248A H253A N255A (mutGS-CT2; SEQ ID NO:22).

In other embodiments, N-terminal and C-terminal fragments of glutamine synthetase are created by splitting the protein at one or more amino acids of the glutamine synthetase protein. In one such aspect of the invention, the N-terminal fragment and/or C-terminal fragments of glutamine synthetase are split at an amino acid of glutamine synthetase selected from the group consisting of: E110, Y104, S125, N126, E264, T111, N105, N126, Q127, and N265.

Similarly, the invention also provides an isolated host cell that has been transfected, transformed or transduced with the vector as described above. The host cell may be selected from the group consisting of CHO, VERO, BHK, HeLa, Cos, MDCK, 293, 3T3, a myeloma cell line, and WI38 cells. One aspect of the invention provides a method of producing a heteromeric complex comprising the step of culturing such a host cell under conditions wherein the heteromeric complex is expressed by the host cell. In one embodiment, the heteromeric complex is an antibody. The inventive methods of claim may also comprise isolating the heteromeric complex.

Still further aspects of the invention include an expression system comprising a first vector encoding a bicistronic transcript comprising a first nucleic acid encoding a desired polypeptide, operably linked to a second nucleic acid encoding an initial mutant subunit of a selectable marker, and a second vector encoding a bicistronic transcript comprising a third nucleic acid, operably linked to a fourth nucleic acid encoding a complementary mutant subunit of a selectable marker, wherein the first and complementary mutant subunits of the selectable marker associate to provide a selectable activity, and wherein the expression system is capable of being transfected into mammalian cells and improving selection of the transfected cells, and further wherein the first nucleic acid encodes an antibody heavy chain and the third nucleic acid encodes an antibody light chain. In one embodiment, the selectable marker is glutamine synthetase.

Still other aspects of the invention include an expression system comprising a first vector encoding a bicistronic transcript comprising a first nucleic acid encoding a desired polypeptide, operably linked to a second nucleic acid encoding an initial fragment of a selectable marker, and a second vector encoding a bicistronic transcript comprising a third nucleic acid, operably linked to a fourth nucleic acid encoding a complementary fragment of a selectable marker, wherein the first and complementary fragments of the selectable marker associate to provide a selectable activity, and wherein the expression system is capable of being transfected into mammalian cells and improving selection of the transfected cells, and further wherein the first nucleic acid encodes an antibody heavy chain and the third nucleic acid encodes an antibody light chain. In one embodiment, the selectable marker is glutamine synthetase.

In one such aspect of the invention, the glutamine synthetase comprises two complementary mutations; thus, the mutGS-NT comprises two or more mutations selected from the group consisting of W60A N61A D63A D63R S66A and D76A and the mutGS-CT comprises one or more mutations selected from the group consisting of E134A E136A E196A E203A N248A H253A N255A R319A and R324A. In one embodiment, mutGS-NT is selected from the group consisting of W60A N61A D63A (mutGS-NT1; SEQ ID NO:6), W60A N61A D63A S66A (mutGS-NT2; SEQ ID NO:10) W60A N61A D63A S66A D76A (mutGS-NT3; SEQ ID NO:25), and W60A N61A D63R S66A (mutGS-NT4; SEQ ID NO:19); and the mutGS-CT is selected from the group consisting of E134A E136A E196A E203A (mutGS-CT1; SEQ ID NO:21) and N248A H253A N255A (mutGS-CT2; SEQ ID NO:22).

In other such embodiments, N-terminal and C-terminal fragments of glutamine synthetase are created by splitting the protein at one or more amino acids of the glutamine synthetase protein. In one such aspect of the invention, the N-terminal fragment and/or C-terminal fragments of glutamine synthetase are split at an amino acid of glutamine synthetase selected from the group consisting of: E110, Y104, S125, N126, E264, T111, N105, N126, Q127, and N265.

The invention also provides an isolated host cell that has been transfected, transformed or transduced with the vector as described above. The host cell may be selected from the group consisting of CHO, VERO, BHK, HeLa, Cos, MDCK, 293, 3T3, a myeloma cell line, and WI38 cells. One aspect of the invention provides a method of producing a heteromeric complex comprising the step of culturing such a host cell under conditions wherein the heteromeric complex is expressed by the host cell. In one embodiment, the heteromeric complex is an antibody. The inventive methods of claim may also comprise isolating the heteromeric complex.

BRIEF DESCRIPTION OF THE DRAWINGS

FIG. 1 is a schematic representation of the nucleic acid constructs utilized in Examples 1-5, each comprising a subunit of a selectable marker and expressing different polypeptides, which can associate to form a heteromeric complex in a cell. Abbreviations are as follows: muGS, mutant glutamine synthetase; Ampr, ampicillin resistance.

DETAILED DESCRIPTION OF THE INVENTION

Figure 1A:
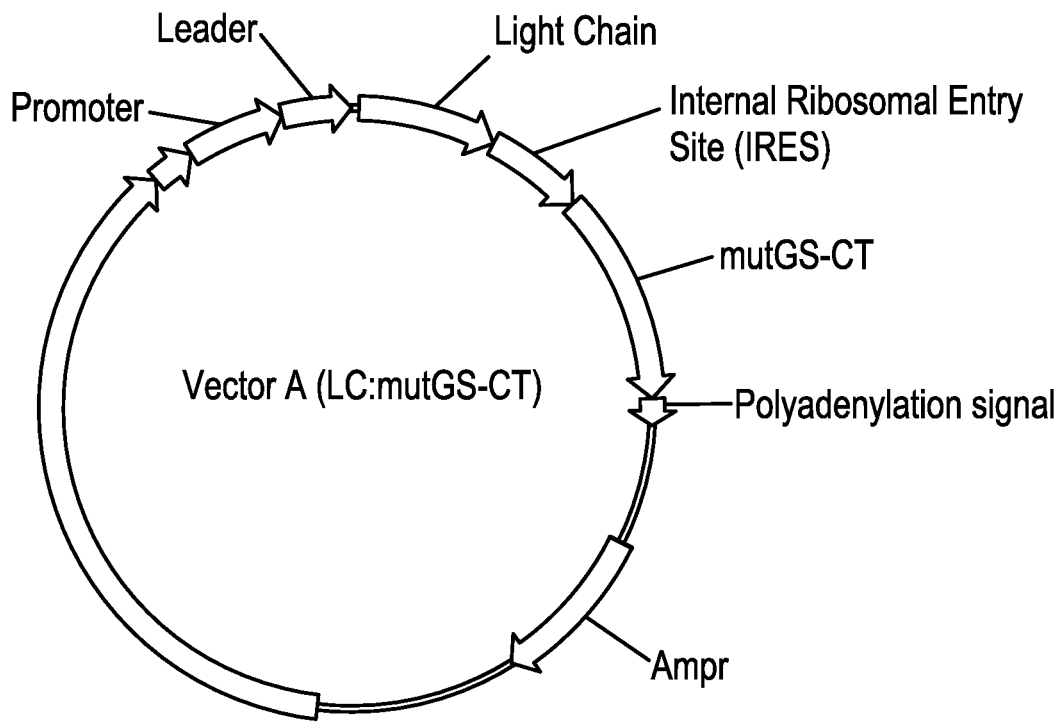
FIG. 1(A) depicts vector A (LC:mutGS-CT)

Efficient production of recombinant heteromeric complexes in cells is improved if each component of the complex is expressed in proportional and high amounts. The present invention improves selection of transfected cells by providing methods and compositions to select for recombinantly engineered cells which express more than one heterologous polypeptide in proportional quantities, such that the polypeptides can efficiently associate to form a heteromeric complex at higher expression levels than traditionally prepared heteromeric complexes. The present invention is also advantageous in that it decreases the time required to select for cells expressing high levels of a desired recombinant heteromeric polypeptide complex, another aspect of improving selection of transfected cells provided by the present invention.

While the terminology used in this application is standard within the art, definitions of certain terms are provided herein to assure clarity and definiteness in the meaning of the claims. Units, prefixes, and symbols may be denoted in their SI (International System of Units) accepted form. Numeric ranges recited herein are inclusive of the numbers defining the range and include and are supportive of each integer within the defined range. The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990).

The disclosed methods are applicable to adherent culture or suspension cultures grown in stirred tank reactors (including traditional batch and fed-batch cell cultures, which may but need not comprise a spin filter), perfusion systems (including alternating tangential flow ("ATF") cultures, acoustic perfusion systems, depth filter perfusion systems, and other systems), hollow fiber bioreactors (HFB, which in some cases may be employed in perfusion processes) as well as various other cell culture methods (see, e.g., Tao et al., (2003) *Biotechnol. Bioeng.* 82:751-65; Kuystermans & Al-Rubeai, (2011) "Bioreactor Systems for Producing Antibody from Mammalian Cells" in *Antibody Expression and Production*, Cell Engineering 7:25-52, Al-Rubeai (ed) Springer; Catapano et al., (2009) "Bioreactor Design and Scale-Up" in *Cell and Tissue Reaction Engineering: Principles and Practice*, Eibl et al. (eds) Springer-Verlag, incorporated herein by reference in their entireties).

As used herein, the terms "a" and "an" mean one or more unless specifically indicated otherwise. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The instant disclosure provides methods of modulating the properties of cell cultures expressing a "protein of interest;" "protein of interest" includes naturally occurring proteins, recombinant proteins, and engineered proteins (e.g., proteins that do not occur in nature and which have been designed and/or created by humans). A protein of interest can, but need not be, a protein that is known or suspected to be therapeutically relevant. Particular examples of a protein of interest include antigen binding proteins (as described and defined herein), peptibodies (i.e., a molecule comprising peptide(s) fused either directly or indirectly to other molecules such as an Fc domain of an antibody, where the peptide moiety specifically binds to a desired target; the peptide(s) may be fused to either an Fc region or inserted into an Fc-Loop, or a modified Fc molecule, for example as described in U.S. Patent Application Publication No. US2006/0140934 incorporated herein by reference in its entirety), fusion proteins (e.g., Fc fusion proteins, wherein a Fc fragment is fused to a protein or peptide, including a peptibody), cytokines, growth factors, hormones and other naturally occurring secreted proteins, as well as mutant forms of naturally occurring proteins.

The term "heteromeric complex" is meant to include a molecular complex formed by the association of at least two different molecules. The association can be non-covalent interaction or covalent attachment, e.g., disulfide bonds. The two different molecules are typically two different polypeptides, however, the invention contemplates heteromeric complexes between polypeptides and nucleic acids and between different nucleic acids. In one embodiment, the heteromeric complex provides a functional activity, such as, the ability to bind a substrate (e.g., an immunoglobulin capable of binding a corresponding antigen), enzymatic activity or the like. In one embodiment, the heteromeric complex of the invention is secreted into the culture medium of the host cell in which it is being produced.

As used herein, the terms "associating" or "interacting" are meant to describe a relationship between at least two molecules wherein one molecule binds to the others and/or affects the activity of the others. Interaction can include the direct or indirect binding of two polypeptides (or polypeptide and nucleic acid), or the functional activation or inhibition of a molecule's activity by another molecule.

In a particular embodiment, the heteromeric complex is an immunoglobulin molecule. The immunoglobulin in vertebrate systems is an antibody comprised of two identical light chains and two identical heavy chains. The four chains are joined together by disulfide bonds, such that each light chain is joined with a heavy chain and the heavy chains are connected across their tails altogether forming a Y-shaped heteromeric complex. Numerous techniques are known by which DNA encoding immunoglobulin molecules can be manipulated to yield DNAs capable of encoding recombinant proteins such as antibodies with enhanced affinity, or other antibody-based polypeptides (see, for example, Larrick et al. (1989), Biotechnology 7:934-938; Reichmann et al. (1988), Nature 332:323-327; Roberts et al. (1987), Nature 328:731-734; Verhoeyen et al. (1988), Science 239:1534-1536; Chaudhary et al. (1989), Nature 339:394-397).

Recombinant cells producing human antibodies (such as are prepared using antibody libraries, and/or transgenic animals, and optionally further modified in vitro), as well as humanized antibodies can also be used in the invention. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger et al., WO 86/01533; Neuberger et al., European Patent No. 0,194,276 B1; Winter, U.S. Pat. No. 5,225,539; Winter, European Patent No. 0,239,400 B1; Queen et al., European Patent No. 0,451,216 B1; and Padlan et al., European Patent No. 0,519,596 A1. For example, the invention can be used to induce the expression of human and/or humanized antibodies that immunospecifically recognize specific cellular targets, e.g., the human EGF receptor, the her-2/neu antigen, the CEA antigen, Prostate Specific Membrane Antigen (PSMA), CDS, CD11a, CD18, NGF, CD20, CD45, Ep-cam, other cancer cell surface molecules, TNF-alpha, TGF-b 1, VEGF, other cytokines, alpha 4 beta 7 integrin, IgEs, viral proteins (for example, cytomegalovirus), etc., to name just a few.

Examples of heteromeric complexes, in addition to immunoglobulins, include but are not limited to any heterodimeric or hetero-oligomeric protein, e.g., BMP2/BMP7, osteogenic protein, interleukin 1 converting enzyme (ICE), various interleukin receptors (e.g., the IL-18 receptor, IL-13 receptor, IL-4 receptor and IL-7 receptor), receptors of the nucleus such as retinoid receptors, T-cell receptors, integrins such as cell adhesion molecules, integrins, tumor necrosis factor receptor and soluble and membrane bound forms of class I and class II major histocompatibility complex proteins (MHC). For heteromeric complexes that are receptors, the invention encompasses both soluble and membrane bound forms of the polypeptides. Descriptions of additional heteromeric proteins that can be produced according to the invention can be found in, for example, Human Cytokines: Handbook for Basic and Clinical Research, Vol. II (Aggarwal and Gutterman, eds. Blackwell Sciences, Cambridge Mass., 1998); Growth Factors: A Practical Approach (McKay and Leigh, Eds. Oxford University Press Inc., New York, 1993) and The Cytokine Handbook (A W Thompson, ed.; Academic Press, San Diego Calif.; 1991).

As used herein, the term "fusion protein" refers to a protein, or domain of a protein (e.g., a soluble extracellular domain) fused to a heterologous protein or peptide. Examples of such fusion proteins include proteins expressed as a fusion with a portion of an immunoglobulin molecule, proteins expressed as fusion proteins with a zipper moiety, and novel polyfunctional proteins such as fusion proteins of cytokines and growth factors (i.e., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins. Any of the molecules herein described can be expressed as a fusion protein including but not limited to the extracellular domain of a cellular receptor molecule, an enzyme, a hormone, a cytokine, a portion of an immunoglobulin molecule, a zipper domain, and an epitope.

The term "antigen binding protein" is used in its broadest sense and means a protein comprising a portion that binds to an antigen or target and, optionally, a scaffold or framework portion that allows the antigen binding portion to adopt a conformation that promotes binding of the antigen binding protein to the antigen. Examples of antigen binding proteins include a human antibody; a humanized antibody; a chimeric antibody; a recombinant antibody; a single chain antibody; a diabody; a triabody; a tetrabody; a Fab fragment; a F(ab')$_2$ fragment; an IgD antibody; an IgE antibody; an IgM antibody; an IgG1 antibody; an IgG2 antibody; an IgG3 antibody; or an IgG4 antibody, and fragments thereof. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, e.g., Korndorfer et al., 2003, *Proteins: Structure, Function, and Bioinformatics*, 53(1): 121-129 (2003); Roque et al., *Biotechnol. Prog.* 20:639-654 (2004). In addition, peptide antibody mimetics ("PAMs") can be used, as well as scaffolds based on antibody mimetics utilizing fibronectin components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain can be done in accordance with the definitions of Kabat et al. in Sequences of Proteins of Immunological Interest, $5^{th}$ Ed., US Dept. of Health and Human Services, PHS, NIH, NIH Publication no. 91-3242, (1991). As desired, the CDRs can also be redefined according an alternative nomenclature scheme, such as that of Chothia (see Chothia & Lesk, (1987) *J. Mol. Biol.* 196:901-917; Chothia et al., (1989) *Nature* 342:878-883 or Honegger & Pluckthun, (2001) *J. Mol. Biol.* 309:657-670).

In the context of the instant disclosure an antigen binding protein is said to "specifically bind" or "selectively bind" its target antigen when the dissociation constant ($K_D$) is $\leq 10^{-8}$ M. The antibody specifically binds antigen with "high affinity" when the $K_D$ is $\leq 5\times 10^{-9}$ M, and with "very high affinity" when the $K_D$ is $\leq 5\times 10^{-10}$ M.

The term "antibody" includes reference to both glycosylated and non-glycosylated immunoglobulins of any isotype or subclass or to an antigen-binding region thereof that competes with the intact antibody for specific binding, unless otherwise specified. Additionally, the term "antibody" refers to an intact immunoglobulin or to an antigen binding portion thereof that competes with the intact antibody for specific binding, unless otherwise specified. Antigen binding portions can be produced by recombinant DNA techniques or by enzymatic or chemical cleavage of intact antibodies and can form an element of a protein of interest. Antigen binding portions include, inter alia, Fab, Fab', F(ab')$_2$, Fv, domain antibodies (dAbs), fragments including complementarity determining regions (CDRs), single-chain antibodies (scFv), chimeric antibodies, diabodies, triabodies, tetrabodies, and polypeptides that contain at least a portion of an immunoglobulin that is sufficient to confer specific antigen binding to the polypeptide.

The term "antibody" refers to a molecule in which the structure and/or function is/are based on the structure and/or function of an antibody, e.g., of a full-length or whole immunoglobulin molecule and/or is/are drawn from the variable heavy chain (VH) and/or variable light chain (VL) domains of an antibody or fragment thereof. An antibody construct is hence capable of binding to its specific target or antigen. Furthermore, the binding domain of an antibody construct according to the invention comprises the minimum structural requirements of an antibody which allow for the target binding. This minimum requirement may e.g. be defined by the presence of at least the three light chain CDRs (i.e. CDR1, CDR2 and CDR3 of the VL region) and/or the three heavy chain CDRs (i.e. CDR1, CDR2 and CDR3 of the VH region), preferably of all six CDRs. An alternative approach to define the minimal structure requirements of an antibody is the definition of the epitope of the antibody within the structure of the specific target, respectively, the protein domain of the target protein composing the epitope region (epitope cluster) or by reference to an specific antibody competing with the epitope of the defined antibody. The antibodies on which the constructs according to the invention are based include for example monoclonal, recombinant, chimeric, deimmunized, humanized and human antibodies.

A Fab fragment is a monovalent fragment having the $V_L$, $V_H$, $C_L$ and $C_H1$ domains; a F(ab')2 fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; a dAb fragment has a $V_H$ domain, a $V_L$ domain, or an antigen-binding fragment of a $V_H$ or $V_L$ domain; an isolated complementarity determining region (CDR); and a single chain Fv (scFv) (U.S. Pat. Nos. 6,846, 634, 6,696,245, U.S. App. Pub. Nos. 05/0202512, 04/0202995, 04/0038291, 04/0009507, 03/0039958, Ward et al., (1989) *Nature* 341:544-546).

A single-chain antibody (scFv) is an antibody in which a VL and a VH region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., *Science* 242:423-26 (1988) and Huston et al., (1988) *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., (1993) *Proc. Natl. Acad. Sci. USA* 90:6444-48; and Poljak et al., (1994) *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Furthermore, the term "antibody" includes monovalent, bivalent and polyvalent/multivalent constructs and, thus, bispecific constructs, specifically binding to only two antigenic structure, as well as polyspecific/multispecific constructs, which specifically bind more than two antigenic structures, e.g. three, four or more, through distinct binding domains. Moreover, the term "antibody" includes molecules consisting of only one polypeptide chain as well as molecules consisting of more than one polypeptide chain, which chains can be either identical (homodimers, homotrimers or homo oligomers) or different (heterodimer, heterotrimer or heterooligomer). Examples for the above identified antibodies and variants or derivatives thereof are described inter alia in Harlow and Lane, Antibodies a laboratory manual, CSHL Press (1988) and Using Antibodies: a laboratory manual, CSHL Press (1999), Kontermann and Dad, Antibody Engineering, Springer, 2nd ed. 2010 and Little, Recombinant Antibodies for Immunotherapy, Cambridge University Press 2009.

The term "bispecific" as used herein refers to an antibody which is "at least bispecific", i.e., it comprises at least a first binding domain and a second binding domain, wherein the first binding domain binds to one antigen or target (here: the target cell surface antigen), and the second binding domain binds to another antigen or target. Accordingly, bispecific antibody constructs comprise specificities for at least two different antigens or targets. Bispecific antibodies may also encompass multispecific antibody constructs such as trispecific antibody constructs, the latter ones including three binding domains, or constructs having more than three (e.g. four, five . . . ) specificities.

One or more CDRs can be incorporated into a molecule either covalently or noncovalently to make it an antigen binding protein. An antigen binding protein can incorporate the CDR(s) as part of a larger polypeptide chain, can covalently link the CDR(s) to another polypeptide chain, or can incorporate the CDR(s) noncovalently. The CDRs permit the antigen binding protein to specifically bind to a particular antigen of interest.

An antigen binding protein can have one or more binding sites. If there is more than one binding site, the binding sites can be identical to one another or can be different. For example, a naturally occurring human immunoglobulin typically has two identical binding sites, while a "bispecific" or "bifunctional" antibody has two different binding sites.

For purposes of clarity, and as described herein, it is noted that an antigen binding protein can, but need not, be of human origin (e.g., a human antibody), and in some cases will comprise a non-human protein, for example a rat or murine protein, and in other cases an antigen binding protein can comprise a hybrid of human and non-human proteins (e.g., a humanized antibody).

A protein of interest can comprise a human antibody. The term "human antibody" includes all antibodies that have one or more variable and constant regions derived from human immunoglobulin sequences. In one embodiment, all of the variable and constant domains are derived from human immunoglobulin sequences (a fully human antibody). Such antibodies can be prepared in a variety of ways, including through the immunization with an antigen of interest of a mouse that is genetically modified to express antibodies derived from human heavy and/or light chain-encoding genes, such as a mouse derived from a Xenomouse®, UltiMab™, or Velocimmune® system. Phage-based approaches can also be employed.

Alternatively, a protein of interest can comprise a humanized antibody. A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. Examples of how to make humanized antibodies can be found in U.S. Pat. Nos. 6,054,297, 5,886,152 and 5,877,293.

An "Fc" region, as the term is used herein, comprises two heavy chain fragments comprising the $C_H2$ and $C_H3$ domains of an antibody. The two heavy chain fragments are held together by two or more disulfide bonds and by hydrophobic interactions of the $C_H3$ domains. Proteins of interest comprising an Fc region, including antigen binding proteins and Fc fusion proteins, form another aspect of the instant disclosure.

A "hemibody" is an immunologically functional immunoglobulin construct comprising a complete heavy chain, a complete light chain and a second heavy chain Fc region paired with the Fc region of the complete heavy chain. A linker can, but need not, be employed to join the heavy chain Fc region and the second heavy chain Fc region. In particular embodiments a hemibody is a monovalent form of an antigen binding protein disclosed herein. In other embodiments, pairs of charged residues can be employed to associate one Fc region with the second Fc region. A hemibody can be a protein of interest in the context of the instant disclosure.

The term "host cell" means a cell that has been genetically engineered to express a polypeptide of commercial or scientific interest. Genetically engineering the cell line involves transfecting, transforming or transducing the cells with a nucleic acid encoding a recombinant polynucleotide molecule (a "gene of interest"), and/or otherwise altering (e.g., by homologous recombination and gene activation or fusion of a recombinant cell with a non-recombinant cell) so as to cause the host cell to express a desired recombinant polypeptide. Methods and vectors for genetically engineering cells and/or cell lines to express a polypeptide of interest are well known to those of skill in the art; for example, various techniques are illustrated in *Current Protocols in Molecular Biology*, Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., *Large Scale Mammalian Cell Culture,* 1990, pp. 15-69. The term includes the progeny of the parent cell, whether or not the progeny is identical in morphology or in genetic make-up to the original parent cell, so long as the gene of interest is present. A cell culture can comprise one or more host cells.

The term "hybridoma" means a cell or progeny of a cell resulting from fusion of an immortalized cell and an antibody-producing cell. The resulting hybridoma is an immortalized cell that produces antibodies. The individual cells used to create the hybridoma can be from any mammalian source, including, but not limited to, hamster, rat, pig, rabbit, sheep, goat, and human. The term also encompasses trioma cell lines, which result when progeny of heterohybrid myeloma fusions, which are the product of a fusion between human cells and a murine myeloma cell line, are subsequently fused with a plasma cell. The term is meant to include any immortalized hybrid cell line that produces antibodies such as, for example, quadromas (see, e.g., Milstein et al., (1983) *Nature,* 537:3053).

The terms "culture" and "cell culture" are used interchangeably and refer to a cell population that is maintained in a medium under conditions suitable to survival and/or growth of the cell population. As will be clear to those of ordinary skill in the art, these terms also refer to the combination comprising the cell population and the medium in which the population is suspended.

The terms "polypeptide" and "protein" (e.g., as used in the context of a protein of interest or a polypeptide of interest) are used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Polypeptides and proteins can be produced by a naturally-occurring and non-recombinant cell, or polypeptides and proteins can be produced by a genetically-engineered or recombinant cell. Polypeptides and proteins can comprise molecules having the amino acid sequence of a native protein, or molecules having deletions from, additions to, and/or substitutions of one or more amino acids of the native sequence.

The terms "polypeptide" and "protein" encompass molecules comprising only naturally occurring amino acids, as well as molecules that comprise non-naturally occurring amino acids. Examples of non-naturally occurring amino acids (which can be substituted for any naturally-occurring amino acid found in any sequence disclosed herein, as desired) include (without limitation): 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, G-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992) Mammalian cells may be cultured in suspension or while attached to a solid substrate. Fluidized bed bioreactors, hollow fiber bioreactors, roller bottles, shake flasks, or stirred tank bioreactors, with or without microcarriers, can be used. In one embodiment 500 L to 2000 L bioreactors are used. In one embodiment, 1000 L to 2000 L bioreactors are used.

The term "cell culturing medium" (also called "culture medium," "cell culture media," "tissue culture media,") refers to any nutrient solution used for growing cells, e.g., animal or mammalian cells, and which generally provides at least one or more components from the following: an energy source (usually in the form of a carbohydrate such as glucose); one or more of all essential amino acids, and generally the twenty basic amino acids, plus cysteine; vitamins and/or other organic compounds typically required at low concentrations; lipids or free fatty acids; and trace elements, e.g., inorganic compounds or naturally occurring elements that are typically required at very low concentrations, usually in the micromolar range.

The nutrient solution may optionally be supplemented with additional optional components to optimize growth of cells, such as hormones and other growth factors, e.g., insulin, transferrin, epidermal growth factor, serum, and the like; salts, e.g., calcium, magnesium and phosphate, and buffers, e.g., HEPES; nucleosides and bases, e.g., adenosine, thymidine, hypoxanthine; and protein and tissue hydrolysates, e.g., hydrolyzed animal or plant protein (peptone or peptone mixtures, which can be obtained from animal byproducts, purified gelatin or plant material); antibiotics, e.g., gentamycin; cell protectants or surfactants such as Pluronic® F68 (also referred to as Lutrol® F68 and Kolliphor® P188; nonionic triblock copolymers composed of a central hydrophobic chain of polyoxypropylene (poly(propylene oxide)) flanked by two hydrophilic chains of polyoxyethylene (poly(ethylene oxide)); polyamines, e.g., putrescine, spermidine and spermine (see e.g., WIPO Publication No. WO 2008/154014) and pyruvate (see e.g. U.S. Pat. No. 8,053,238) depending on the requirements of the cells to be cultured and/or the desired cell culture parameters.

Cell culture media include those that are typically employed in and/or are known for use with any cell culture process, such as, but not limited to, batch, extended batch, fed-batch and/or perfusion or continuous culturing of cells.

A "base" (or batch) cell culture medium refers to a cell culture medium that is typically used to initiate a cell culture and is sufficiently complete to support the cell culture.

A "growth" cell culture medium refers to a cell culture medium that is typically used in cell cultures during a period of exponential growth, a "growth phase", and is sufficiently complete to support the cell culture during this phase. A growth cell culture medium may also contain selection agents that confer resistance or survival to selectable markers incorporated into the host cell line. Such selection agents include, but are not limited to, geneticin (G4118), neomycin, hygromycin B, puromycin, zeocin, methionine sulfoximine, methotrexate, glutamine-free cell culture medium, cell culture medium lacking glycine, hypoxanthine and thymidine, or thymidine alone.

A "production" cell culture medium refers to a cell culture medium that is typically used in cell cultures during the transition when exponential growth is ending and protein production takes over, "transition" and/or "product" phases, and is sufficiently complete to maintain a desired cell density, viability and/or product titer during this phase.

A "perfusion" cell culture medium refers to a cell culture medium that is typically used in cell cultures that are maintained by perfusion or continuous culture methods and is sufficiently complete to support the cell culture during this process. Perfusion cell culture medium formulations may be richer or more concentrated than base cell culture medium formulations to accommodate the method used to remove the spent medium. Perfusion cell culture medium can be used during both the growth and production phases.

Concentrated cell culture medium can contain some or all of the nutrients necessary to maintain the cell culture; in particular, concentrated medium can contain nutrients identified as or known to be consumed during the course of the production phase of the cell culture. Concentrated medium may be based on just about any cell culture media formulation. Such a concentrated feed medium can contain some or all the components of the cell culture medium at, for example, about 2×, 3×, 4×, 5×, 6×, 7×, 8×, 9×, 10×, 12×, 14×, 16×, 20×, 30×, 50×, 100×, 200×, 400×, 600×, 800×, or even about 1000× of their normal amount.

The components used to prepare cell culture medium may be completely milled into a powder medium formulation;

partially milled with liquid supplements added to the cell culture medium as needed; or added in a completely liquid form to the cell culture.

Cell cultures can also be supplemented with independent concentrated feeds of particular nutrients which may be difficult to formulate or are quickly depleted in cell cultures. Such nutrients may be amino acids such as tyrosine, cysteine and/or cystine (see e.g., WIPO Publication No. 2012/145682). In one embodiment, a concentrated solution of tyrosine is independently fed to a cell culture grown in a cell culture medium containing tyrosine, such that the concentration of tyrosine in the cell culture does not exceed 8 mM. In another embodiment, a concentrated solution of tyrosine and cystine is independently fed to the cell culture being grown in a cell culture medium lacking tyrosine, cystine or cysteine. The independent feeds can begin prior to or at the start of the production phase. The independent feeds can be accomplished by fed batch to the cell culture medium on the same or different days as the concentrated feed medium. The independent feeds can also be perfused on the same or different days as the perfused medium.

"Serum-free" applies to a cell culture medium that does not contain animal sera, such as fetal bovine serum. Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kan.), among others. Serum-free versions of such culture media are also available. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

The term "bioreactor" means any vessel useful for the growth of a cell culture. The cell cultures of the instant disclosure can be grown in a bioreactor, which can be selected based on the application of a protein of interest that is produced by cells growing in the bioreactor. A bioreactor can be of any size so long as it is useful for the culturing of cells; typically, a bioreactor is sized appropriate to the volume of cell culture being grown inside of it. Typically, a bioreactor will be at least 1 liter and may be 2, 5, 10, 50, 100, 200, 250, 500, 1,000, 1500, 2000, 2,500, 5,000, 8,000, 10,000, 12,000 liters or more, or any volume in between. The internal conditions of the bioreactor, including, but not limited to pH and temperature, can be controlled during the culturing period. Those of ordinary skill in the art will be aware of, and will be able to select, suitable bioreactors for use in practicing the present invention based on the relevant considerations.

"Cell density" refers to the number of cells in a given volume of culture medium. "Viable cell density" refers to the number of live cells in a given volume of culture medium, as determined by standard viability assays (such as trypan blue dye exclusion method).

The term "cell viability" means the ability of cells in culture to survive under a given set of culture conditions or experimental variations. The term also refers to that portion of cells which are alive at a particular time in relation to the total number of cells, living and dead, in the culture at that time.

"Packed cell volume" (PCV), also referred to as "percent packed cell volume" (% PCV), is the ratio of the volume occupied by the cells, to the total volume of cell culture, expressed as a percentage (see Stealer, et al., (2006) Biotechnol Bioeng. December 20:95(6):1228-33). Packed cell volume is a function of cell density and cell diameter; increases in packed cell volume could arise from increases in either cell density or cell diameter or both. Packed cell volume is a measure of the solid content in the cell culture. Solids are removed during harvest and downstream purification. More solids mean more effort to separate the solid material from the desired product during harvest and downstream purification steps. Also, the desired product can become trapped in the solids and lost during the harvest process, resulting in a decreased product yield. Since host cells vary in size and cell cultures also contain dead and dying cells and other cellular debris, packed cell volume is a more accurate way to describe the solid content within a cell culture than cell density or viable cell density. For example, a 2000 L culture having a cell density of $50 \times 10^6$ cells/ml would have vastly different packed cell volumes depending on the size of the cells. In addition, some cells, when in a growth-arrested state, will increase in size, so the packed cell volume prior to growth-arrest and post growth-arrest will likely be different, due to increase in biomass as a result to cell size increase.

"Growth-arrest", which may also be referred to as "cell growth-arrest", is the point where cells stop increasing in number or when the cell cycle no longer progresses. Growth-arrest can be monitored by determining the viable cell density of a cell culture. Some cells in a growth-arrested state may increase in size but not number, so the packed cell volume of a growth-arrested culture may increase. Growth-arrest can be reversed to some extent, if the cells are not in declining health, by reversing the conditions that lead to growth arrest.

The term "titer" means the total amount of a polypeptide or protein of interest (which may be a naturally occurring or recombinant protein of interest) produced by a cell culture in a given amount of medium volume. Titer can be expressed in units of milligrams or micrograms of polypeptide or protein per milliliter (or other measure of volume) of medium. "Cumulative titer" is the titer produced by the cells during the course of the culture, and can be determined, for example, by measuring daily titers and using those values to calculate the cumulative titer.

The term "fed-batch culture" refers to a form of suspension culture and means a method of culturing cells in which additional components are provided to the culture at a time or times subsequent to the beginning of the culture process. The provided components typically comprise nutritional supplements for the cells which have been depleted during the culturing process. Additionally or alternatively, the additional components may include supplementary components (e.g., a cell-cycle inhibitory compound). A fed-batch culture is typically stopped at some point and the cells and/or components in the medium are harvested and optionally purified.

The terms "integrated viable cell density" or "IVCD" are used interchangeably and mean the average density of viable cells over the course of the culture multiplied by the amount of time the culture has run.

"Cumulative viable cell density" (CVCD) is calculated by multiplying an average viable cell density (VCD) between two time-points with the time duration between those two time points. CVCD is the area under the curve formed by plotting the VCD versus time.

The invention utilizes selectable markers that can be subject to intragenic complementation to directly select for expression constructs that encode heteromeric proteins, such as antibodies, using a two-vector system. "Intragenic complementation" refers to complementation between pieces of genetic material (i.e., nucleic acids), each of which has a different defect within the same locus. An individual protein encoded by the genetic material is defective and non-functional, but two individual defective proteins may associate to form an active protein. If the individual defective proteins are able to associate and exhibit activity, the individual defective proteins are said to be "complementary." For selectable marker proteins that are made up of multiple identical subunits (such as GS), intragenic complementation can occur when mutant subunits are complementary.

"Intragenic complementation" may also occur between fragments of an individual protein encoded by the genetic material that associate to form an active protein. As described herein, the mature GS enzyme in higher eukaryotes exists as a decameric complex consisting of two pentameric rings. This invention demonstrates that intragenic complementation of GS can be successfully used as part of a selection system for the generation of cell lines expressing recombinant proteins. The utility of the system for high level expression of a recombinant antibody in CHO cells which are genetically modified to be glutamine synthetase deficient.

An individual protein encoded by the genetic material is rendered defective and non-functional by the introduction of one or more mutations in the encoding nucleic acid, which mutation(s) alter the structure of the protein sufficiently to render it non-functional. The mutation or mutations may be introduced by any method that is known in the art of molecular biology. Alternatively, a protein fragment may be used that is rendered defective and non-functional. In such instance, two protein fragments may associate to form an active protein by intragenic complementation.

Nucleic acid molecules are constructed that encode a polypeptide and a mutant subunit of the selectable marker, arranged in such a way that expression of the mutant subunit correlates with expression of the polypeptide. Thus, when the nucleic acid molecules encoding complementary mutant subunits are introduced into cells and selective conditions applied, approximately equal and high levels of expression of each of the complementary mutant subunit will provide the highest selectable activity. In addition, the operably linked polypeptides will be expressed in nearly equal and high amounts, thus optimizing selection of cells expressing equal and high levels of the desired polypeptides.

In one embodiment of the invention, the selectable marker is glutamine synthetase, (GS), the active site of which is located at the junction of two subunits of GS, so co-expression of complementary, functionally-impaired mutant subunits should result in some intact functional active sites. The individual mutant subunits do not have significant selectable activity alone, but do provide selectable activity when co-expressed with their complementary mutant subunit. The optimal activity of the subunits can depend upon their interaction, and as such can be facilitated by interaction domains Such interaction domains can be endogenous to the subunit or it can be heterologous to the subunit. Additional selectable markers that are useful in the present invention include arginosuccinate lyase, adenylosuccinate synthetase, and glutamate dehydrogenase, for which complementary mutants can be identified. For example, intragenic complementation with argininosuccinate lyase mutants can be confirmed by growth in the absence of arginine, while intragenic complementation with adenylosuccinate synthetase mutants can be confirmed by growth in the absence of adenosine.

In one non-limiting embodiment, the invention entails the use of two fragments of a selectable marker, each of which may be expressed as a fusion protein to an interaction domain. When expressed, the interaction domain promotes association or dimerization of the two fragments thereby allowing the subunits to function and providing a selectable activity (e.g., but not limited to, that described by Pelletier et al. (1998), Proc. Natl. Acad. Sci., 95:12141-12146). Suitable selective markers include GS and the other selectable markers described above, as well as selectable markers such as those that confer resistance to particular drugs that are ordinarily toxic, and metabolic enzymes that confer cell survival or induce cell death under prescribed conditions, as disclosed herein.

An "interaction domain" is a domain, including but not limited to, polypeptides capable of facilitating the interaction or association of two or more homologous or heterologous polypeptides In one embodiment, the interaction domain is a dimerization domain. A dimerization domain can be a polypeptide capable of inducing interaction or association of two polypeptides. There are two types of dimers, those capable of forming homodimers (with the same sequence), or heterodimers (with another sequence).

In one illustrative but non-limiting embodiment, the interaction domain is a leucine zipper coiled coil polypeptide. A leucine zipper typically comprises about 35 amino acids containing a characteristic seven residue repeat with hydrophobic residues at the first and fourth residues of the repeat (Harbury et al. (1993), Science 262:1401). Thus a leucine zipper is amenable to fusion to a polypeptide for the purpose of oligomerizing the polypeptide as it is a small molecule and is less likely to disrupt the polypeptides normal function than would a larger interaction domain. Examples of leucine zippers include but are not limited leucine zipper domains from polypeptides such as GCN4, C/EBP, c-Fos, c-Jun, c-Myc and c-Max.

Additional examples of dimerization domains include helix-loop-helix domains (Murre et al. (1989), Cell 58:537-544). The retinoic acid receptor, thyroid hormone receptor, other nuclear hormone receptors (Kurokawa et al. (1993), Genes Dev. 7:1423-1435) and yeast transcription factors GAL4 and HAP1 (Marmonstein et al. (1992), Nature 356:408-414; Zhang et al. (1993), Proc. Natl. Acad. Sci. USA 90:2851-2855; U.S. Pat. No. 5,624,818) all have dimerization domains with this motif.

In yet another embodiment, the interaction domain is a tetramerization domain, which is a polypeptide capable of binding three other tetramerization domains to form a tetrameric complex. Examples of proteins containing tetramerization domains include but are not limited to the *E. coli* lactose repressor (amino acids 46-360; Chakerian et al. (1991), J. Biol. Chem. 266:1371; Alberti et al. (1993), EMBO J. 12:3227; and Lewis et al. (1996), Nature 271:1247), and the p53 tetramerization domain at residues 322-355 (Clore et al. (1994), Science 265:386; Harbury et al. (1993), Science 262:1401; U.S. Pat. No. 5,573,925).

In an alternative embodiment, the invention entails the use of three subunits of a selectable marker, each expressed as a fusion protein to an interaction domain, thereby enhancing association to provide a selectable activity. In this embodiment, there are three components of the heteromeric complex. In the expressed vector(s) coding sequences for each are operably linked to coding sequences for each of the respective subunits of the selectable marker, for example, a bispecific antibody expressing a single heavy chain and two different light chains, wherein the two light chains are both capable of associating with the heavy chain. The invention also encompasses use of selectable markers known or yet to be disclosed that have four or even more subunits.

The present invention will also be useful in preparing heteromultimeric (or hetero-oligomeric) proteins that comprise three or more subunits such as those that are described previously herein. This include bispecific antibodies, and other heteromultimeric proteins that are known in the art For example, a bispecific antibody can be expressed by using a first selectable marker that is capable of intragenic complementation as described herein (for example, GS) to express the heavy chain and light chain from a first antibody, and a different selectable marker such as a split metabolic enzyme or resistance marker, or a second selectable marker that is different than the first selectable marker and is capable of intragenic complementation, to express the heavy chain and light chain of a second antibody that is capable of associating with the first antibody to form a bispecific antibody.

Alternatively, the first selectable marker that is capable of intragenic complementation as described herein (for example, GS) can be used to express two different heavy chains of a bispecific antibody, where the heavy chains are capable of associating with each other. The light chains can then be expressed using a different selectable marker. In some cases, the light chain may be identical for both arms of the bispecific antibody, indicating that a single selectable marker (a metabolic enzyme or resistance marker, or other form of selectable marker) can be used for expression of the light chains. Alternatively, a different light chain may associate with each different heavy chain of the bispecific antibody, in which case a different selectable marker such as a split metabolic enzyme or resistance marker, or a second selectable marker that is different than the first selectable marker and is capable of intragenic complementation, is used to express the first and second light chains.

As will be shown below in the examples, it has been discovered that the methods and compositions of the invention reduce the amount of time necessary to select for the desired cells expressing high levels of a heteromultimeric protein. Thus, in yet another embodiment, the invention encompasses selecting for cells expressing high levels of a recombinant polypeptide, particularly heteromultimeric polypeptides. Additionally, the invention finds particular utility in improving the production of heteromeric complexes via cell culture processes.

In some embodiments, the nucleic acids encoding the mutant marker subunits are fused in frame to a nucleic acid encoding a linker, which is then fused in frame to a nucleic acid encoding an interaction domain. Linkers can include any relatively short, flexible sequence that allows the interaction domain to interact and for the subunits to function to provide a selectable activity. Examples of linkers are abundant in the relevant art and can comprise GGPGG, GPGGG, where in single letter amino acid codes, G is glycine and P is proline. In one embodiment, the linker is a series of glycine and serine residues, for example, that described by Curtis et al. (1991; Proc Natl Acad Sci 88(13):5809-5813).

In one embodiment, the two complementary mutant subunits are expressed from two vectors, wherein the first vector comprises a first nucleic acid encoding a first polypeptide, and wherein the first nucleic acid is operably linked to a second nucleic acid encoding a mutant subunit of a selectable marker. The second vector comprises a third nucleic acid encoding a polypeptide that is capable of associating with the first polypeptide encoded by the first nucleic acid, wherein the third nucleic acid is operably linked to a fourth nucleic acid encoding a complementary mutant subunit of the selectable marker. Thus, both vectors are simultaneously introduced into a cell population and selection for intragenic complementation is applied.

In another embodiment, two complementary fragments are expressed from two vectors, wherein the first vector comprises a first nucleic acid encoding a first polypeptide, and wherein the first nucleic acid is operably linked to a second nucleic acid encoding a fragment of a selectable marker. The second vector comprises a third nucleic acid encoding a polypeptide that is capable of associating with the first polypeptide encoded by the first nucleic acid, wherein the third nucleic acid is operably linked to a fourth nucleic acid encoding a complementary fragment of the selectable marker. Thus, both vectors are simultaneously introduced into a cell population and selection for intragenic complementation is applied.

For example, a two-vector system to express an antibody is constructed by preparing a first vector comprising a first nucleic acid encoding one chain of the antibody, wherein the first nucleic acid is operably linked to a second nucleic acid encoding a mutGS-NT. The second vector comprises a third nucleic acid encoding the other chain of the antibody, wherein the third nucleic acid is operably linked to a fourth nucleic acid encoding a mutGS-CT. Thus, in one embodiment, the first nucleic acid encodes an immunoglobulin heavy chain and the third nucleic acid encodes an immunoglobulin light chain. Alternatively, the first nucleic acid encodes an immunoglobulin light chain and the third nucleic acid encodes an immunoglobulin heavy chain.

In another embodiment, two complementary fragments are expressed from two vectors, wherein the first vector comprises a first nucleic acid encoding a first polypeptide, and wherein the first nucleic acid is operably linked to a second nucleic acid encoding a fragment of a selectable marker. The second vector comprises a third nucleic acid encoding a polypeptide that is capable of associating with the first polypeptide encoded by the first nucleic acid, wherein the third nucleic acid is operably linked to a fourth nucleic acid encoding a complementary fragment of the selectable marker. Thus, both vectors are simultaneously introduced into a cell population and selection for intragenic complementation is applied.

In such instance, a two-vector system to express an antibody is constructed by preparing a first vector comprising a first nucleic acid encoding one chain of the antibody, wherein the first nucleic acid is operably linked to a second nucleic acid encoding an N-terminal glutamine synthetase fragment. The second vector comprises a third nucleic acid encoding the other chain of the antibody, wherein the third nucleic acid is operably linked to a fourth nucleic acid encoding a C-terminal glutamine synthetase fragment. Thus, in one embodiment, the first nucleic acid encodes an immunoglobulin heavy chain and the third nucleic acid encodes an immunoglobulin light chain. Alternatively, the first nucleic acid encodes an immunoglobulin light chain and the third nucleic acid encodes an immunoglobulin heavy chain.

Additional embodiment include the use of one or more IRES allowing expression of one or both of the mutGS subunits. "IRES" means, in the context of this invention, an internal ribosome entry site that facilitates the initiation of translation of an mRNA from an internal site (i.e., a site other than the 5'end of the mRNA).

One example of a suitable IRES is the IRES of encephalomyocarditis virus (ECMV), as described in Jang and Wimmer Genes & Development 4 1560 (1990) and Jang, Davies, Kaufman and Wimmer J. Vir. 63 1651 (1989). The residues 335-848 of EMCV form a suitable IRES; other variants or portions of ECMV IRES are known and will be suitable for use in the present invention. A suitable portion or variant of an IRES is one that will confer sufficient translation of the second open reading frame (ORF).

Additionally, the 3' end of an IRES may be altered (or mutated) to reduce the efficiency of translation, thereby providing a means to enhance selection and/or amplification methods. For example, the efficiency of the IRES can be decreased by using a sequence previously shown to allow efficient selection and amplification (Aldrich et al., *Biotechnol Prog* 19, 1433; 2003). Alternative sequences are known, or can be determined by one of ordinary skill in the art.

In another embodiment, the invention further comprises a nucleic acid encoding a different functional selectable marker, in addition to a subunit of a selectable marker and a polypeptide of a heteromeric complex. For purposes herein, a "different functional selectable marker" is not a mutant subunit of the selectable marker that is capable of intragenic complementation, but is a protein with different selectable activity. Well known markers such as zeomycin, neomycin, puromycin, Blasticidin S, or GPT which confers resistance to mycophenolic acid, etc., can be used as different functional selectable markers. Additionally, complementary mutants of a different selectable marker that is capable of intragenic complementation can also be used.

In this embodiment, the invention comprises two vectors, wherein each of the vectors comprises a first nucleic acid encoding a polypeptide that can form a heteromeric complex operably linked to a second nucleic acid encoding at least one mutant subunit of a selectable marker, as well as also a nucleic acid encoding a different, functional selectable marker. Further, the respective polypeptides encoded by the first nucleic acid of each vector can associate to form a complex, and the subunit or subunits encoded by the second nucleic acids of each vector can associate to provide a selectable activity and the polypeptides encoded by the third nucleic acids provide selectable activities different than the selectable activity of the subunits encoded by the second nucleic acids.

For example, the first vector can encode resistance to neomycin and the second vector can encode resistance to zeomycin or only one vector can contain the additional different functional selectable marker. Thus, one vector is transfected into a cell line and selection is applied (i.e., the drug G418 is added to neomycin resistant cells). After selection, conventional methods can be used to determine the presence of the vector and the expression level of the polypeptides encoded by the nucleic acids on the vector, for example by PCR, Southern blot, ELISA, western blot, and the like. Once high level expression has been obtained, the second vector is transfected into the cell line. While maintaining selection for the first vector, selection is applied for the second selectable marker (i.e., zeomycin resistance) and the presence of the second vector and expression of the respective vector encoded proteins are assessed. In this embodiment, once it has been determined that both vectors are present, selection is applied for expression of the subunits that have associated in the cell to provide a selectable activity as described herein.

In an alternative embodiment, both the nucleic acids of the invention encoding independent selectable activities are transfected simultaneously and selection is applied at the same time. Once it has been determined that both vectors are present, selection is applied for expression of the subunits that have associated in the cell to provide a selectable activity, as described above.

In yet another embodiment, the vectors of the invention encoding independent selectable activities are each transfected into separate cell lines. Once selection is applied and clones have been identified that express high levels of the proteins encoded by each desired vector, the cells are fused as described in Hori et al. (U.S. Pat. No. 5,916,771). Once fusion is complete, selection is applied for the selectable activity provided by the subunits.

In yet another embodiment, nucleic acids of the invention optionally not containing an independent selectable activity are transfected simultaneously with a third vector. The third vector encodes for a separate selectable activity, such as for example, neomycin resistance or beta galactosidase that can allow for a preliminary selection of cells that were successfully transfected. Once this preliminary selection has been performed, selection can be applied for the selectable activity of the mutant subunits. In this embodiment, equal quantities of the two expression vectors are transfected while the third vector is transfected at one-third the concentration of the first two vectors (e.g., a ratio of 3:3:1 or 6:6:1 or the like). One of skill in the art will recognize that variations in the ratios are within the scope of the invention.

The nucleic acids encoding a component of the desired heteromeric complex can be obtained as a cDNA or as a genomic DNA by methods known in the art. For example, messenger RNA coding for a desired component can be isolated from a suitable source employing standard techniques of RNA isolation, and the use of oligo-dT cellulose chromatography to segregate the poly-A mRNA. When the heteromeric complex to be expressed is an antibody, suitable sources of desired nucleic acids can be isolated from mature B cells or a hybridoma culture. In addition, the nucleic acids for use in the invention can be obtained by chemical synthesis.

In addition to the nucleic acid encoding the desired component of the heteromeric complex, vector constructs can include additional components to facilitate replication in prokaryotic and/or eukaryotic cells, integration of the construct into a eukaryotic chromosome, and markers to aid in selection of and/or screening for cells containing the construct. Vectors of the invention are recombinant DNA vectors including, but not limited to, plasmids, phages, phagemids, cosmids, viruses, retroviruses, and the like, which insert a desired nucleic acid into a cell.

A nucleic acid is "operably linked" when it is placed into a functional relationship with another nucleic acid. More specifically, operably linked means that two different nucleic acids encoding different polypeptides have transcription induced simultaneously. Operably linked is also intended to mean that the linked nucleic acids can be contiguous in a single transcriptional unit, while translation is directed from one or more ribosomal start sites (e.g., internal ribosomal entry site). Operably linked transcriptional units that encode two different polypeptides are referred to as "bicistronic transcripts."

The methods of the invention also can be used in combination with known or yet to be discovered methods of inducing the production of recombinant proteins. By "inducing conditions" is meant a technique to increase the relative production per cell of a desired recombinant protein. Such techniques include cold temperature shift, and additions of chemicals, and combinations of any known or yet to be discovered techniques, to name just a few examples, as well as any yet to be described and/or discovered induction techniques. Typically, a batch or a perfusion culture of cells at high density is induced to produce the recombinant protein. Often, other cell processes (such as growth and division) are inhibited so as to direct most of the cells' energy into recombinant protein production.

Any selectable marker having subunits can be used in the methods and compositions of the invention. As used herein, the term "subunit" when referring to a selectable marker refers to a portion of a selectable marker. Further, a first mutant subunit (referred to herein as an "initial mutant subunit") of a selectable marker can be expressed with a second complementary mutant subunit (referred to herein as a "complementary mutant subunit") of the same selectable marker to provide a level of selectable activity not present in either mutant subunit alone. A subunit can also refer to a polypeptide having mutations that are complemented by another mutated polypeptide that is also a different subunit of the selectable marker.

Selectable markers that confer resistance to particular drugs that are ordinarily toxic to an animal cell can be used in the methods and compositions of the invention. For example, the following are non-limiting examples of resistance selectable markers: zeomycin (zeo); puromycin (PAC); Blasticidin S (BlaS), GPT, which confers resistance to mycophenolic acid (Mulligan & Berg (1981), Proc. Natl. Acad. Sci. USA 78:2072); the neomycin resistance gene, which confers resistance to the aminoglycoside G-418 (Colberre-Garapin et al. (1981), J. Mol. Biol. 150:1); and hygro, which confers resistance to hygromycin (Santerre et al. (1984), Gene 30:147).

Metabolic enzymes that confer cell survival or induce cell death under prescribed conditions can also be used in the methods and compositions of the inventions. Examples include but are not limited to: dihydrofolate reductase (DHFR); herpes simplex virus thymidine kinase (TK) (Wigler et al. (1977), Cell 11:223), hypoxanthine-guanine phosphoribosyltransferase (HGPRT) (Szybalska & Szybalski (1962), Proc. Natl. Acad. Sci. USA 48:2026), and adenine phosphoribosyltransferase (APRT) (Lowy et al. (1980), Cell 22:817), which are genes which can be employed in cells lacking TK, HGPRT or APRT, respectively.

In one embodiment, glutamine synthetase (GS) is the selectable marker used in the methods and compositions of the present invention. GS comprises two stacked pentameric rings of identical subunits with ten active sites formed by N-terminal residues from one subunit and C-terminal residues from the adjacent subunit. N-terminal (mutGS-NT) and C-terminal (mutGS-CT) mutant constructs are prepared and evaluated for complementation. Neither the mutGS-NT nor the mutGS-CT will allow cell growth in medium lacking glutamine, however, when GS mutant cells are transfected with both constructs, those cells transfected with both constructs at similar levels survive in media lacking glutamine. When co-transfection with two such mutants occurs, the mutants are referred to as "complementary." Alternatively, cells expressing endogenous GS can be used and transfectants can be selected by conferring increased resistance to toxic levels of methionine sulfoximine (MSX).

Selectable markers that are based on color selection can also be used in the methods and compositions of the invention. In a particular example, beta-galactosidase can be used (Blau et al., WO 98/44350). Fluorescence markers can also be used in the methods of the present invention, for example, GFP has been used for clonal selection of cells to measure protein interactions in protein-fragment complementation assays (Remy and Michnick (1999), Proc. Natl. Acad. Sci., 96:5394-5399). Similarly fluorescein-conjugated methotrexate can be used to detect cells expressing complementing DHFR fragments (Remy and Michnick (2001), Proc. Natl. Acad. Sci., 98:7678-83). An advantage for fluorescent markers is that this selection can be done in any animal cell type and is not restricted to those having a deficiency in a metabolic pathway or does not require a drug sensitivity, e.g., to neomycin.

As used herein, the term "polypeptide" includes naturally occurring or recombinantly expressed proteins, including pre- and post-translational processing, or fragments thereof, which typically retain secondary structure. Proteins are large molecules with high molecular weights (from about 10,000 for small ones [of 50-100 amino acids] to more than 1,000,000 for certain forms); they are composed of varying amounts of the same 20 amino acids, which in the intact protein are united through covalent chemical linkages called peptide bonds. The amino acids, linked together, form linear unbranched polymeric structures called polypeptide chains; such chains can contain hundreds of amino acid residues; these are arranged in specific order for a given species of protein. The term "peptide" includes short fragments of polypeptides or proteins, of typically less than 20 amino acids in length.

The term "cell culture" is meant to include the growth and propagation of cells outside of a multicellular organism or tissue. Typically, cell culture is performed under sterile, controlled temperature and atmospheric conditions in tissue culture plates (e.g., 10-cm plates, 96 well plates, etc.), or other adherent culture (e.g., on microcarrier beads) or in suspension culture such as in roller bottles. Cultures can be grown in shake flasks, small scale bioreactors, and/or large-scale bioreactors. A bioreactor is a device used to culture cells in which environmental conditions such as temperature, atmosphere, agitation, and/or pH can be monitored and adjusted. A number of companies (e.g., ABS Inc., Wilmington, Del.; Cell Trends, Inc., Middletown, Md.) as well as university and/or government-sponsored organizations (e.g., The Cell Culture Center, Minneapolis, Minn.) offer cell culture services on a contract basis.

Optimal periods for which the cultures are in contact with agents that select for the selectable activity are for longer than the typical period for one normal growth cycle (e.g., for Chinese hamster ovary cells (CHO cells), where one growth cycle has been reported to be approximately 20-22 hours (Rasmussen et al. (1998), Cytotechnology, 28:31-42)). As such, in one embodiment, the cultures comprise selectable conditions, e.g., drugs, metabolites, or color substrates, preferably for at least about one day, more preferably for at least about 3 days, and even more preferably for at least about 7 days.

A wide variety of animal cell lines suitable for growth in culture are available from, for example, the American Type Culture Collection (ATCC, Manassas, Va.) and NRRL (Peoria, Ill.). Some of the more established cell lines typically used in the industrial or academic laboratory include CHO, VERO, BHK, HeLa, Cos, CV1, MDCK, 293, 3T3, PC12, mycloma (e.g., NSO), and WI38 cell lines, to name but a few examples. In other embodiments, non-animal cell lines can be used in the methods of the invention, for example, plant cell lines, insect cell lines (e.g., sf9), yeast cells or bacterial cells such as E. coli.

In one embodiment, the GS-deficient CHO cells such as CHOZN® GS-/-ZFN-modified CHO cells (Sigma Aldrich Fine Chemicals, St. Louis Mo.) are used. GS-deficient CHO cells (or other mammalian cells) can also be prepared using methods that are known in the art. Additionally, CHO cells are easy to manipulate as adherent or suspension cultures and exhibit relatively good genetic stability. In addition, new animal cell lines can be established using methods well known by those skilled in the art (e.g., by transformation, viral infection, and/or selection).

As noted above, a variety of host-expression vector systems can be utilized to express the heteromeric complexes of the invention. Where the heteromeric complex is soluble, the peptide or polypeptide can be recovered from the culture, i.e., from the host cell in cases where the heteromeric complexes are not secreted, and from the culture media in cases where the heteromeric complexes are secreted by the cells. However, the expression systems also encompass engineered host cells that express the heteromeric complexes anchored in the cell membrane.

Purification or enrichment of the heteromeric complexes from such expression systems can be accomplished using appropriate detergents and lipid micelles and methods well known to those skilled in the art. However, such engineered host cells themselves can be used in situations where it is important not only to retain the structural and functional characteristics of the heteromeric complexes, but also to assess biological activity, e.g., in drug screening assays.

The protein expressed by the methods of the invention can be collected. In addition the protein can be purified, or partially purified, from such culture or component (e.g., from culture medium or cell extracts or bodily fluid) using known processes. The phrase "partially purified" means that some fractionation procedure, or procedures, have been carried out, but that more polypeptide species (at least 10%) than the desired protein is present. By "purified" is meant that the protein is essentially homogeneous, i.e., less than 1% contaminating proteins are present. Fractionation procedures can include but are not limited to one or more steps of filtration, centrifugation, precipitation, phase separation, affinity purification, gel filtration, ion exchange chromatography, size exclusion chromatography (SEC), hydrophobic interaction chromatography (HIC; using such resins as phenyl ether, butyl ether, or propyl ether), HPLC, or some combination of above.

The invention also optionally encompasses further formulating the proteins. By the term "formulating" is meant that the proteins can be buffer exchanged, sterilized, bulk-packaged and/or packaged for a final user. For purposes of the invention, the term "sterile bulk form" means that a formulation is free, or essentially free, of microbial contamination (to such an extent as is acceptable for food and/or drug purposes), and is of defined composition and concentration.

The term "sterile unit dose form" means a form that is appropriate for the customer and/or patient administration or consumption. Such compositions can comprise an effective amount of the protein, in combination with other components such as a physiologically acceptable diluent, carrier, or excipient. The term "physiologically acceptable" means a non-toxic material that does not interfere with the effectiveness of the biological activity of the active ingredient(s).

For the present invention, sets of inactivating mutations that encode changes in the N-terminus (mutGS-NT) of the mammalian GS protein as well as sets of inactivating mutations that encode changes in the C-terminus (mutGS-CT) of the protein were developed. The GS catalytic site was subject to an alanine scan in which mutations were made, individually and in combinations, to all the evolutionarily-conserved alanine residues that are involved in binding of glutamate, ATP, and/or ammonia. The majority of residues were selected based on evidence from published X-ray crystallographic and biochemical studies of GS enzymes, but all residues within 4.5 Å of the substrates/ligands/metals in the active site were evaluated as potential candidates. Combinations of the N-terminal and the C-terminal catalytically-impaired, but structurally-intact, GS mutants were identified, and evaluated for the ability to complement one another to restore some GS activity when co-expressed.

A two-vector system was constructed by linking expression of one chain of an antibody with a mutGS-NT or N-terminal GS fragment and another with a mutGS-CT or C-terminal GS fragment. One expression vector with a promoter/enhancer driving expression of an antibody heavy chain (HC) on a single mRNA with an IRES allowing expression of a mutGS-NT or N-terminal GS fragment was constructed. Separately, the expression of the light chain (LC) of the antibody was linked to mutGS-CT or C-terminal GS fragment by constructing a vector with a promoter/enhancer driving expression of the LC and an IRES allowing expression of mutGS-CT or C-terminal GS fragment. Neither the mutGS-NT nor mutGS-CT, N-terminal or C-terminal GS fragments, by themselves allowed cell growth in medium lacking glutamine. However, when GS mutant cells were transfected with both constructs, those cells transfected with both constructs at similar levels allowed survival in media lacking glutamine. Those cells also produced similar amounts of the LC and the HC for the antibody of interest. The stringency of selection can be further increased by reducing the efficiency of the IRES, resulting in reduced translation of the mutGS selectable marker, or potentially by adding the GS inhibitor, L-methionine sulfoximine (MSX).

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

Example 1

This example describes the selection and preparation of murine glutamine synthetase (GS) mutants identified as being likely to be useful in intragenic complementation. Four N-terminal residues of murine GS (W60, N61, D63, and S66) and 11 C-terminal residues (E134, E136, E196, E203, N248, H253, N255, R319, R324, E338 and R340) were selected for evaluation in an alanine mutation scan. Individual and combination mutant constructs were generated in pcDNA3.3 vectors (neomycin resistance, Invitrogen Grand Island, N.Y.), resulting in a total of 9 N-terminal mutant constructs and 16 C-terminal mutant constructs.

The mutant constructs were evaluated for expression of intact GS protein in CHO-K1 cell lines. The cells were cultured in non-selective chemically-defined growth media containing glutamine in vented shake-flasks at 36° C., 5% $CO_2$, 70% relative humidity and shaken at 150-160 rpm in humidified incubators. Viable cell density (VCD) and viability were measured with a ViCell automated cell counter (Beckman-Coulter, Inc., Brea, Calif.). Cultures were passaged by dilution every 3-4 days.

One million cells per condition were transfected with 10 micrograms linearized DNA by electroporation (biological triplicates). DNA was linearized with PvuI-HF restriction enzyme (New England Biolabs, Ipswich, Mass.) overnight at 37° C. according to manufacturer's recommendations. Agarose gel electrophoresis was used to confirm complete linearization of each plasmid. After restriction digest, DNA was precipitated overnight at −70° C. by adding 10% reaction volume of 3M sodium acetate and 200% reaction volume of 100% ethanol to each digest. Following ethanol precipitation, DNA was pelleted, pellets washed with once with 70% ethanol, air-dried and resuspended in HEPES-buffered saline. DNA concentrations were measured on NanoDrop 2000 (Thermo Scientific, Wilmington, Del.) and adjusted to 1 microgram/microliter with HEPES-buffered saline.

For intragenic complementation testing, 5 micrograms of each of the two plasmids along with 10 micrograms sheered salmon sperm DNA (Invitrogen) were used. Transfections were set up by spinning down 1 million cells per condition from day 3 growth cultures, resuspending the cells in 150 microliters HEPES-buffered saline, adding a total of 10 micrograms of plasmid DNA (5 micrograms of each plasmid and 10 micrograms and transferring the mixture into wells of a 96-well electroporation plate (Bio-Rad Laboratories, Inc., Hercules, Calif.).

Electroporation was performed using in 96-well plates using the Gene Pulser MXcell™ (Bio-Rad Laboratories, Inc., Hercules, Calif.) with the following settings: exponential wave, voltage=290 V, capacitance=950 microF, resistance=950 ohms. Following electroporation, the cells were transferred into 2 ml/well pre-warmed non-selective growth medium in vented 24 deep-well plates (24 DWPs) and shaken at 220 rpm in humidified Kühner incubators (Kühner AG, Basel, Switzerland).

Three days after transfection, the cells were counted and transferred into selective medium (chemically-defined growth media lacking glutamine) at $1\times10^6$ viable cells/mL. Stable pools were generated by serial passaging of the cells in selective medium every 3-4 days until culture viability recovered above 90%. Cell counts were performed on Guava EasyCyte™ HT flow cytometer (EMD Millipore, Billerica, Mass.) using ViaCount assay module, following 15-minute incubation of cells in reagent (1:10 dilution of culture into ViaCount FLEX reagent (EMD Millipore, Billerica, Mass.) at working concentration (1:50 dilution in PBS)).

All pools were allowed to recover to at least 90% viability prior to testing in functional assays. Following pool generation, Western blot analysis of triplicate pools was performed to establish the level of GS protein overexpression for each construct and determine whether any mutation interfered with production of intact GS protein.

For Western blot analysis, $3\times10^6$ cells were lysed in 100 microliters of RIPA Buffer (Thermo Scientific Pierce, Rockford, Ill.) supplemented with EDTA-free Halt Protease and Phosphatase Inhibitor Cocktail (Thermo Scientific, Rockford, Ill.) for 30 minutes on ice. Lysates were cleared by centrifugation at 13,000 rpm, 4× loading buffer (Invitrogen, Grand Island, N.Y.) was added, and samples were boiled at 95° C. for 5 minutes. 15 µl of each sample were run on E-Page 48 gels (Invitrogen, Grand Island, N.Y.) and transferred to PVDF membranes using an iBlot (Invitrogen, Grand Island, N.Y.). Each membrane was probed with 1:500 mouse anti-Glutamine Synthetase antibody (Cat #610518, BD biosciences, San Jose, Calif.) overnight at 4° C., followed by incubation with 1:2,000 anti-mouse Alexa Fluor 680 secondary antibody (Life Technologies, Grand Island, N.Y.). Blots were scanned on Odyssey Infrared Imaging System (LI-COR, Lincoln, Nebr.) and quantified using ImageJ software.

TABLE 1

Murine Glutamine synthetase mutants tested

| Selected GS mutants (Alanine scan) | Mutant Class | Intact GS protein | Sequence ID |
|---|---|---|---|
| W60A | N-terminal | Yes | 2 |
| N61A | N-terminal | Yes | 3 |
| D63A | N-terminal | Yes | 4 |
| S66A | N-terminal | Yes | 5 |
| W60A N61A D63A (NT1) | N-terminal | Yes | 6 |
| W60A N61A S66A | N-terminal | Yes | 7 |
| W60A D63A S66A | N-terminal | Yes | 8 |
| N61A D63A S66A | N-terminal | Yes | 9 |
| W60A N61A D63A S66A (NT2) | N-terminal | Yes | 10 |
| E134A | C-terminal | Yes | 11 |
| E136A | C-terminal | Yes | 12 |
| E196A | C-terminal | Yes | 13 |
| E203A | C-terminal | Yes | 14 |
| N248A | C-terminal | Yes | 15 |
| H253A | C-terminal | Yes | 16 |
| N255A | C-terminal | Yes | 17 |
| R319A | C-terminal | Yes | 18 |
| R324A | C-terminal | Yes | 20 |
| E134A E136A E196A E203A | C-terminal | Yes | 21 |
| N248A H253A N255A | C-terminal | Yes | 22 |

Although initial analysis indicated amino acid residues E388 and R340 as candidate residues for mutation, overexpression of E388A and R340A GS mutants (as single mutations or in combination with other mutations) did not yield intact GS protein. Therefore, constructs containing these mutations were not considered further.

Since stable mutant GS pools were generated in wild type CHO-K1 parental cell line, which has functional GS enzyme, mutant activity assessment was performed with a growth/viability screen in selective medium lacking glutamine and supplemented with 25 microM of the GS inhibitor, L-methionine sulfoximine (MSX). Wild type CHO-K1 cells died following 4 passages in selective medium. Certain N-terminal and C-terminal mutations prevented culture growth in selective medium, but even growth-impaired pools retained relatively high viability.

Cells transfected with individual GS N-terminal mutants grew similar to the wild type construct, so these constructs were not tested further. However, two N-terminal multiple mutant constructs, W60A N61A D63A (mutGS-NT1; SEQ ID NO:6) and W60A N61A D63A S66A (mutGS-NT2; SEQ ID NO:10) yielded high levels of overexpressed GS protein and performed the closest to the empty vector negative control in the functional assay, and were selected for further analysis. In addition, two other N-terminal mutant constructs, W60A N61A D63A S66A D76A (mutGS-NT3; SEQ ID NO:25), and W60A N61A D63R S66A (mutGS-NT4; SEQ ID NO:19) were prepared in an effort to increase the stringency of the complementation effect, and evaluated. In the latter construct, aspartate-63 was mutated to arginine instead of alanine because the analogous mutant in Anabena azollae completely wiped out biosynthetic activity and was expressed the same as wild type, whereas the mutation to alanine retained 6.5% of biosynthetic activity (Eur. J. Biochem. 266, 1202 (1999) Crespo et al.).

Even though several single C-terminal mutant constructs passed the functional assessment, two constructs that contained multiple mutations, E134A E136A E196A E203A (mutGS-CT1; SEQ ID NO:21) and N248A H253A N255A (mutGS-CT2; SEQ ID NO:22), were selected for further analysis.

Example 2

This example describes the effects of the mutations in GS on the expression of a recombinant heterodimeric protein, i.e., a monoclonal antibody (mAb). Selected N-terminal and C-terminal mutants described in Example 1 were cloned into mAb expression vectors to construct multiple combinations of two-vector systems where expression of the light chain (LC) is linked via an IRES to a mutGS-CT and the heavy chain (HC) is linked to a mutGS-NT. A CHO-K1 GS knock out cell line was constructed using the CompoZr® Knockout ZFN Kit-CHO GS according to the manufacturer's instructions (Sigma-Aldrich St. Louis, Mo.). CHO-K1 glutamine synthetase knock out (CHO-K1 GS-KO) cell lines were cultured as previously described.

Triplicate CHO-K1 GS knockout transfections were performed using the vectors containing mAb LC or HC linked to either the wild type GS (positive control) or selected N- and C-terminal mutants and cultured in medium lacking glutamine. Initial pcDNA3.3 vector containing wild type GS was used as an additional positive control. Both the pcDNA3.3 wild type GS pools and the mAb-linked wild type GS pools recovered above 90% viability by 20 days of passaging in glutamine-free medium. In contrast, mock-transfected pools and all of the mAb-linked mutant GS pools died after 17 days in glutamine-free medium, confirming that selected mutants yield functionally-impaired GS protein product.

Finally, selected N-terminal and C-terminal mutants were evaluated for GS intragenic complementation within the two-vector expression system for generation of mAb-producing pools in CHO-K1 GS knockout cell line. These cells were transfected with intragenic complementation vectors A (LC:mutGS-CT) and B (HC:mutGS-NT) with the indicated mutations in the GS sequence (shown in Table 2 below). All evaluated mutGS-CT/mutGS-NT combinations were able to recover to approximately 90% viability over 25 days of passaging in glutamine-free medium. Two-vector LC:mutGS-CT/HC:mutGS-NT pools had a greater viability drop and took longer to recover in selective medium than the single-vector positive controls containing wild type GS.

Generated triplicate stable pools were further evaluated for mAb expression with a 10-day fed-batch production assay. The production assays were set up from day 4 growth cultures at 1:5 split by dilution into chemically-defined production medium in 24 DWPs (~0.5×10⁶ viable cells/ml). Culture growth and viability was monitored on days 3, 6, 8 and 10 using Guava ViaCount assay (Millipore, Billerica, Mass.). Bolus feeds were performed on days 3, 6 and 8 with chemically-defined feed medium. Media glucose concentration was measured on feed days using colorimetric Poly-Chem (Polymedco, Cortlandt Manor, N.Y.) reagent and adjusted to 12 g/L with a 50% glucose stock solution. End of production titer was determined on Day 10 culture supernatant by affinity High Performance Liquid Chromatography (HPLC) using POROS A/20 Protein A column. All pools generated with the GS intragenic complementation two-vector system containing individual mAb chains linked via IRES to individual GS mutants produced detectable levels of antibody; values are shown in Table 2 (Example 3), below.

Example 3

This example describes a method of increasing antibody titer in transfected pools by increasing the stringency of selection by decreasing the efficiency of the IRES GS junction. The sequence in the initial constructs is wild type EMCV sequence up to the ATG-12 which was fused to the start codon of GS (Davies and Kaufman, *J Virol* 66, 1924; 1992). The efficiency of the IRES was decreased by using a sequence previously shown to allow efficient selection and amplification (Aldrich et al., *Biotechnol Prog* 19, 1433; 2003). The DNA sequence of the junctions in the more efficient (ED3) junction is compared to the DNA sequence of the less efficient junction (317) below. The numbers below the ED3 sequence indicate the ATGs found in the WT EMCV. The last ATG denotes the start codon of GS.

```
                                          (SEQ ID NO:23)
317     GATGATAATACCCTCGAGATCCGTGCCATCATG (SEQ ID NO:24)
ED3     GATGATAATATGGCCACAACCATG
        10       11       12
```

Figure 1B:
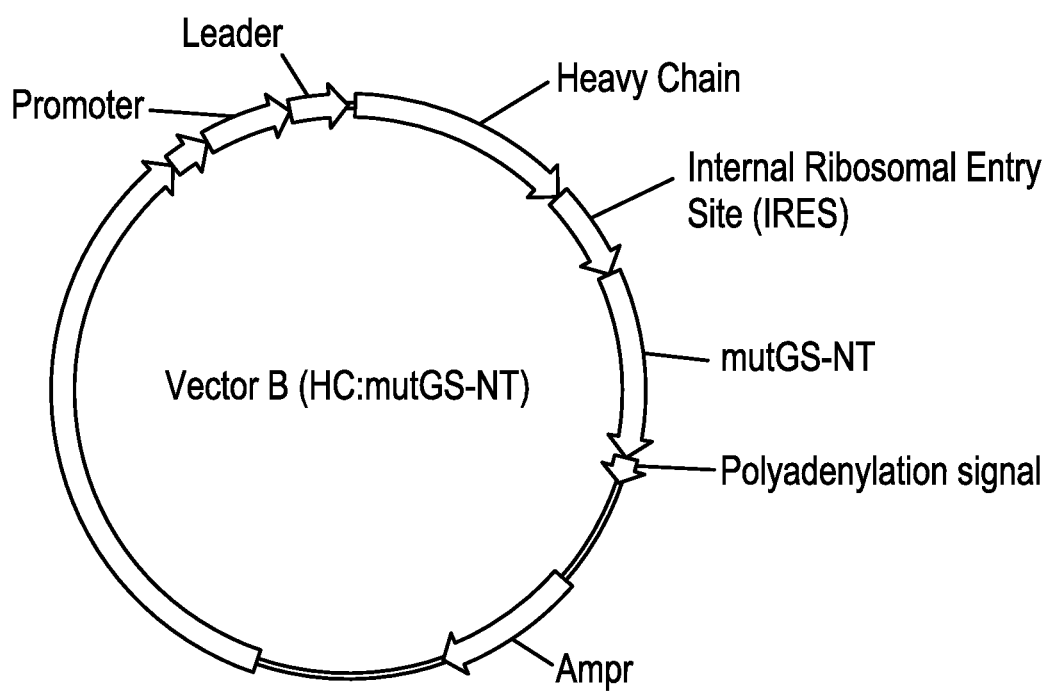
FIG. 1(B) depicts vector B (HC:mutGS-NT).

The expression vectors were identical to those shown in FIG. 1 other than the sequence at the junction of the IRES and GS. Transfection of cells with both plasmids with the less efficient IRES-GS junction resulted in lower viabilities following transfection and longer recovery times. Only two out of three CT1-NT4 transfections recovered and none of the other mutIRES combinations recovered. However, for those mutIRES combinations that did recover, 10-day fed-batch culture yielded 0.55 grams/L for one pool and 0.17 g/L for the other. The specific productivity of these pools was 16 p/c/d and 6.9 p/c/d, respectively. The 0.55 g/L titer exceed those previously reported and do not require FACS sorting to achieve them (Ye, J. et al. *Biotechnol Prog* 26, 1431; 2010).

TABLE 2

Expression of Intragenic GS transfectants with different IRES-GS junctions.

| Construct | Titer Avg (n = 3) g/L | qP Avg (n = 3) p/c/d |
|---|---|---|
| CT1-NT1 | 0.08 | 1.17 |
| CT1-NT2 | 0.05 | 0.76 |
| CT1-NT3 | 0.05 | 0.82 |
| CT1-NT4 | 0.07 | 0.82 |
| CT2-NT1 | 0.04 | 0.59 |
| CT2-NT2 | 0.05 | 0.72 |
| CT2-NT3 | 0.06 | 0.87 |
| CT2-NT4 | 0.04 | 0.56 |
| CT2-NT4 MSX 1 | 0.29 | 9.18 |
| mut IRES CT1-NT4 1 | 0.55 | 15.69 |
| mut IRES CT1-NT4 3 | 0.17 | 6.86 |

The samples labeled CT1-NT1-4 and CT2-NT1-4 all used the pED3 junction (SEQ ID NO:24). The samples labeled mutIRES have the less efficient IRES shown in SEQ ID NO:23.

Example 4

This example describes another strategy to increase the selectivity of these cultures. Transfections were performed as described in Example 2 but during the selection an inhibitor of GS, MSX, was added to the cultures in order to select for higher levels of GS expression. One out of the three CT2-NT4 cultures with the more efficient (i.e., non-mutant) IRES recovered while none of the CT1-NT4 or either of the transfectants with a mutant IRES recovered. For the single culture that recovered, a 10-day fed-batch culture yielded 0.29 grams/L with a specific productivity of 9.18p/c/d (see Table 2 above).

Example 5

This example describes the results from a large number of mut IRES CT1-NT4 transfections. These constructs have the less efficient IRES shown in SEQ ID NO:23. A total of 88 CHO-K1 GS knockout transfections were performed using the vectors containing mut IRES CT1-NT4. A total of 10 out of the 88 transfections survived selection and yielded robustly growing tranfection pools after approximately 25 days of culture and behaved similarly to the smaller number of transfections in example 2. The mock-transfected pools GS pools died after 17 days in glutamine-free medium.

Duplicate stable pools were further evaluated for mAb expression with a 10-day fed-batch production assay. The production assays were set up from day 4 growth cultures seed into chemically-defined production medium in 24 DWPs at $0.6 \times 10^6$ viable cells/ml. Culture growth and viability was monitored on days 3, 6, 8 and 10 using Guava ViaCount assay (Millipore, Billerica, Mass.). Bolus feeds were performed on days 3, 6 and 8 with chemically-defined feed medium. Media glucose concentration was measured on feed days using colorimetric PolyChem (Polymedco, Cortlandt Manor, N.Y.) reagent and adjusted to 12 g/L with a 50% glucose stock solution. End of production titer was determined on Day 10 culture supernatant by affinity High Performance Liquid Chromatography (HPLC) using POROS A/20 Protein A column. All pools generated with the GS intragenic complementation two-vector system containing individual mAb chains linked via IRES to individual GS mutants produced relatively high levels of antibody with two pools averaging over 1 g/L; values are shown in Table 3 below.

TABLE 3

Expression of Intragenic CT1-NT4 GS transfectants mut IRES-GS junctions.

| Construct | Titer Avg (n = 2) g/L | qP Avg (n = 2) p/c/d |
|---|---|---|
| mut IRES CT1-NT4 4 | 0.425 | 14.10 |
| mut IRES CT1-NT4 5 | 0.76 | 13.02 |
| mut IRES CT1-NT4 6 | 0.57 | 11.05 |
| mut IRES CT1-NT4 7 | 1.025 | 11.64 |
| mut IRES CT1-NT4 8 | 0.44 | 6.73 |
| mut IRES CT1-NT4 9 | 1.055 | 11.74 |
| mut IRES CT1-NT4 10 | 0.6 | 12.16 |
| mut IRES CT1-NT4 11 | 0.375 | 7.61 |
| mut IRES CT1-NT4 12 | 0.56 | 7.21 |
| mut IRES CT1-NT4 13 | 0.81 | 14.06 |

Example 6

This example describes a molecular complementation approach for the enzyme glutamine synthetase. The glutamine synthetase enzyme was expressed as two independent fragments and enzyme activity was fully reconstituted by genetic complementation of the two fragments. A series of constructs were created that split the glutamine synthetase enzyme at various residues. These points were based on information from molecular structure of the enzyme. These constructs were tested in a cell based assay for their ability to rescue a cell line which is deficient in glutamine synthetase activity. From this testing several fragments were identified that are able to fully rescue the glutamine synthetase deficient cells and therefore demonstrate that these fragments can associate to create a fully functional glutamine synthetase enzyme.

Much of the previous work on protein fragment complementation has used proteins which exist as functional monomers and whose reassembly only requires the designed fragments. This work demonstrated the ability to use molecular complementation to recapitulate the activity of both the GS monomer and subsequent formation of the decameric functional enzyme complex. Complementing protein fragments were identified by using a molecular modelling approach to look for regions in the GS monomer which would allow for the protein to be split. A GCN4 leucine zipper (LZ) and flexible linker were also added to the separate fragments to aid in reassembly. The fragments tested are shown in Table 4 and the sequence of the murine GS protein used in these studies in shown Table 5. The GS fragments were cloned into a mammalian expression vector and transfected into CHO cells which are deficient in GS activity. These cells can normally only survive in cell culture media supplemented with glutamine. The ability of these constructs to rescue these cells were tested by removal of glutamine from the medium.

TABLE 4

GS Molecular Complementation Fragment Design:

| A - Chain 1 | B - Chain 2 |
|---|---|
| 1. N-terminus -- E110 -- LZ | LZ -- T111 -- C-terminus |
| 2. N-terminus -- Y104 -- LZ | LZ -- N105 -- C-terminus |
| 3. N-terminus -- S125 -- LZ | LZ -- N126 -- C-terminus |
| 4. N-terminus -- N126 -- LZ | Q127 -- C-terminus -- LZ |
| 5. N-terminus -- E264 -- LZ | LZ -- N265 -- C-terminus |

N terminal LZ = MSDRMKQLEDKVEELLSKVYHLENE-VARLKKLVGERGGGGSGGGGGS
C terminal LZ = GGGGSGGGGSSDRMKQLEDKVEELLSKVYHLENE-VARLKKLVGER-STOP

TABLE 5

Sequence of the Mouse GS enzyme used in these studies and highlighted split points

| 1 | MATSASSHLNKGIKQMYMSLPQGEKVQAMYIWVDGTGEGLRC KTRTLDCE |
| 51 | PKCVEELPEWNFDGSSTFQSEGSNSDMYLHPVAMFRDPFRKD PNKLVLCE |
| 101 | VFKYNRKPAETNLRHICKRIMDMVSNQHPWFGMEQEYTLMGT DGHPFGWP |
| 151 | SNGFPGPQGPYYCGVGADKAYGRDIVEAHYRACLYAGVKITG TNAEVMPA |
| 201 | QWEFQIGPCEGIRMGDHLWIARFILHRVCEDFGVIATFDPKP IPGNWNGA |
| 251 | GCHTNFSTKAMREENGLKCIEEAIDKLSKRHQYHIRAYDPKG GLDNARRL |

TABLE 5-continued

Sequence of the Mouse GS enzyme used in these studies and highlighted split points

```
301 TGFHETSNINDFSAGVANRGASIRIPRTVGQEKKGYFEDRRP
    SANCDPYA

351 VTEAIVRTCLLNETGDEPFQYKN*
```

Y 104 E 110 S 125 N 126 E 264

Figure 2:
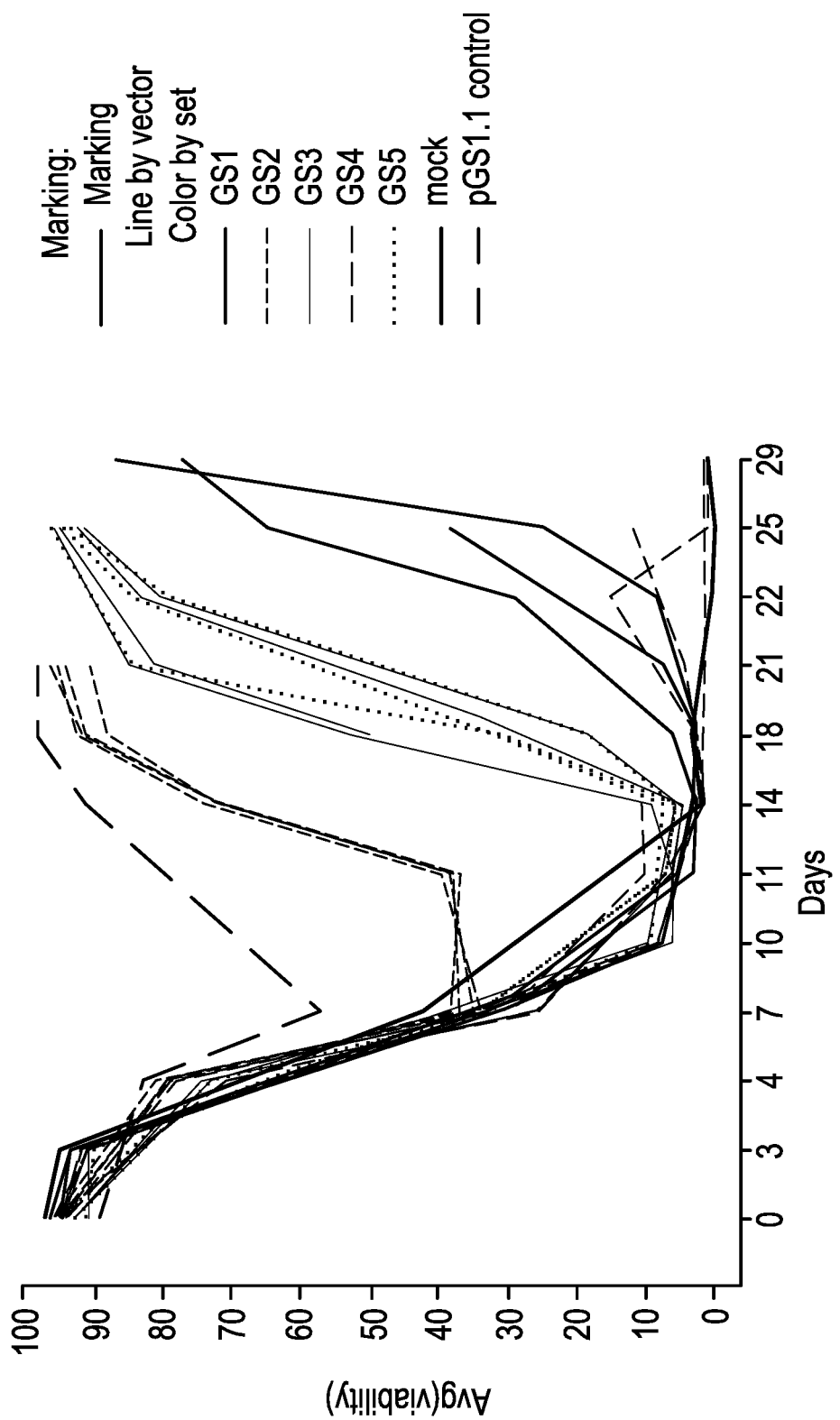
FIG. 2 is a graph showing the results of rescue experiment 1. Constructs A and B for each version (1-5) were transfected into CHO-K1 GS knockout cells and tested for their ability to rescue the cells in glutamine free media. A plasmid expressing full length GS enzyme was used as the control.
Figure 3:
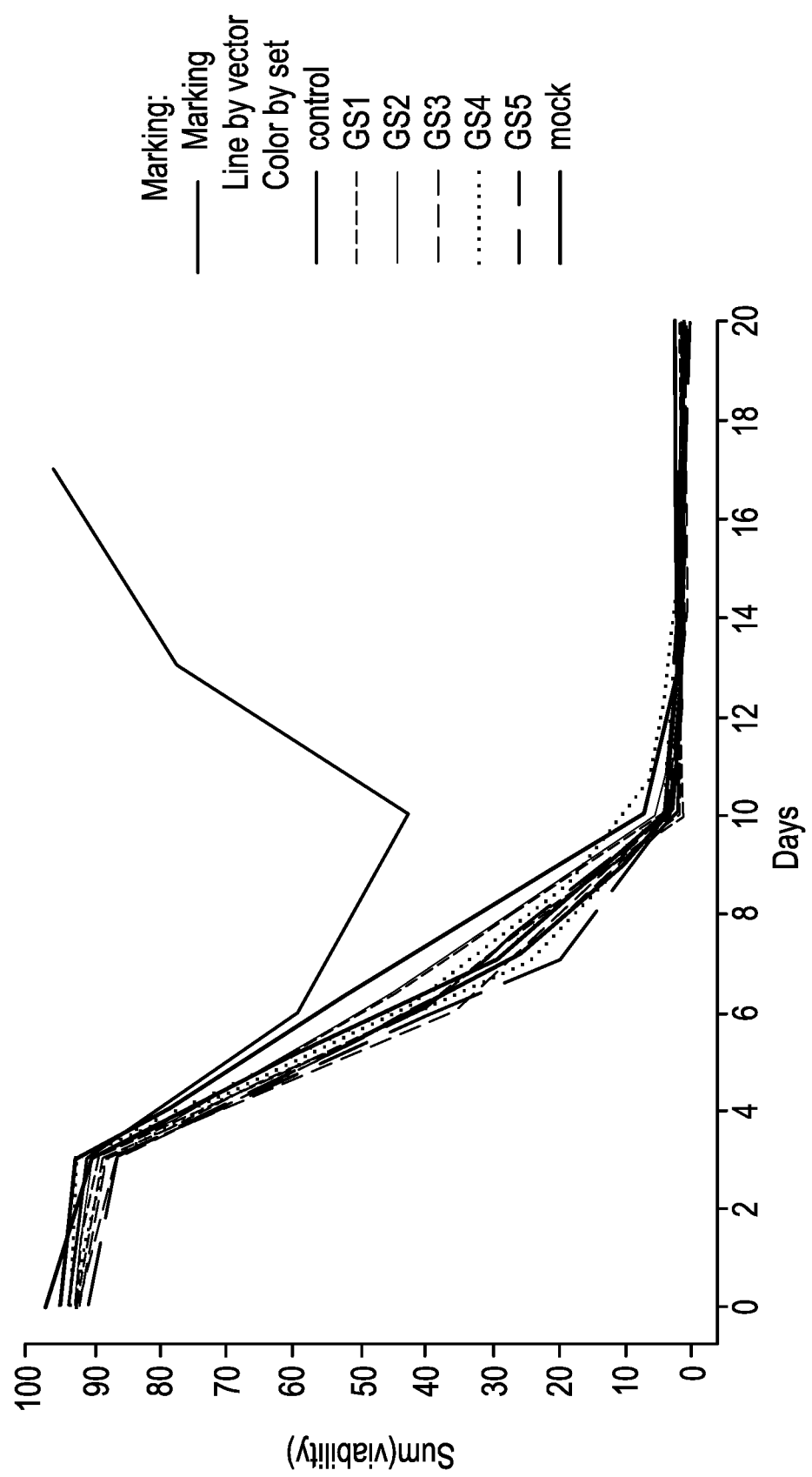
FIG. 3 is a graph showing that none of the A or B fragments alone are able to rescue the KO cell line, confirming that both the fragments are required for GS enzyme activity to be restored.
Figure 4:
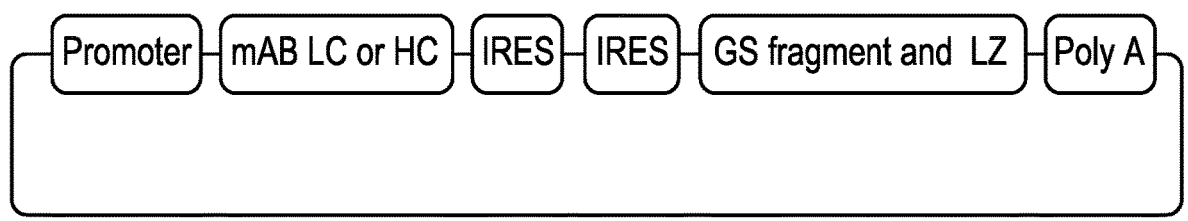
FIG. 4 is a schematic representation of the expression vectors used in Example 6, each containing an antibody light chain or heavy chain, IRES and glutamine synthetase fragment.
Figure 5:
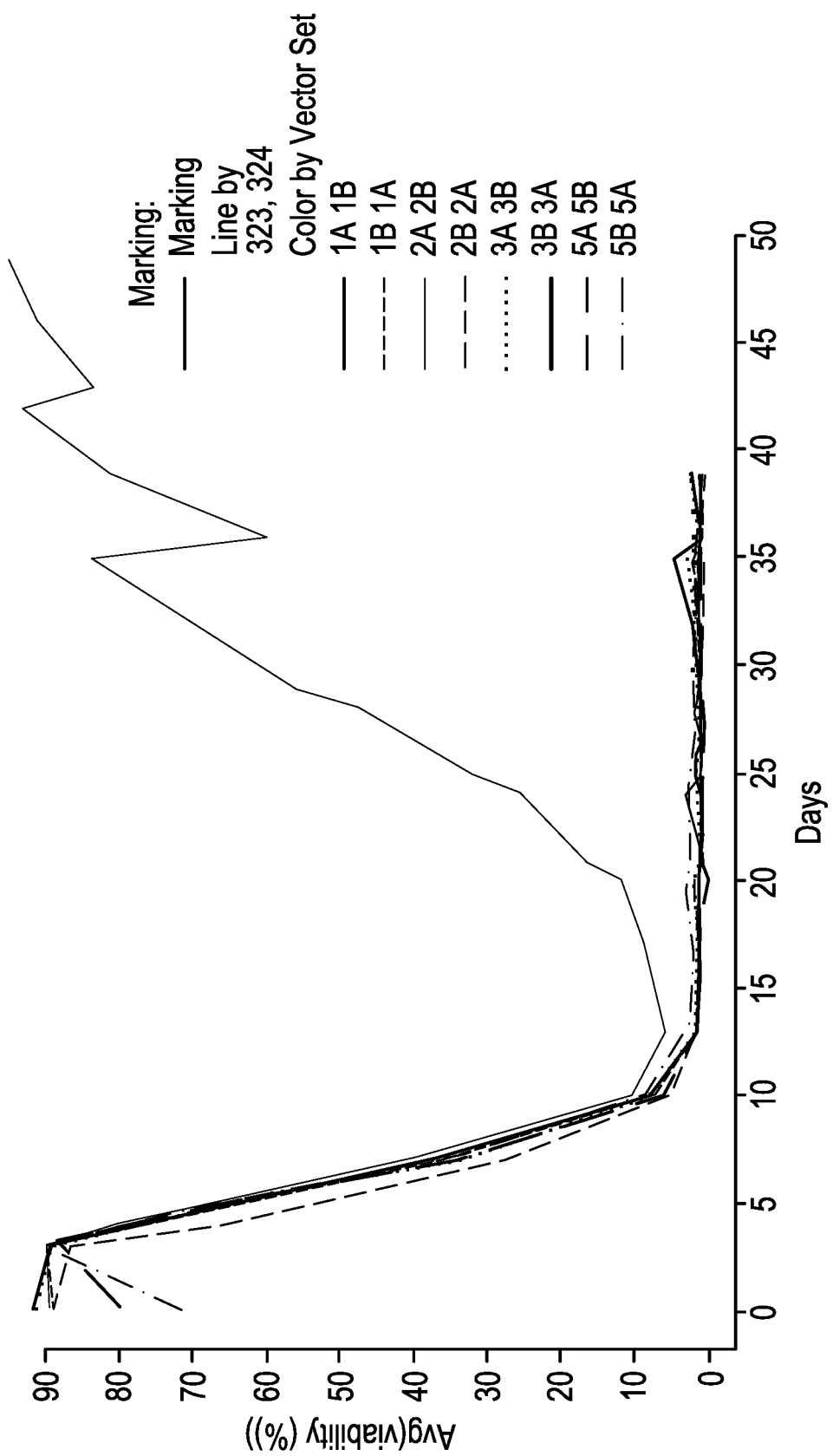
FIG. 5 is a graph showing the use of GS fragment vectors downstream of antibody LC and HC genes. Vector combination 2A-LC and 2B-HC were able to rescue the GS knockout cells.

As shown in FIG. 2, constructs 1, 2, 3 and 5 were able to successfully rescue the glutamine synthetase deficient cells. This demonstrates that these fragments were capable of forming a fully functional glutamine synthetase enzyme in vivo. A summary of the rescue results is shown in Table 6. As a control, it was assessed whether any of the A or B fragments alone were able to rescue the glutamine synthetase deficient cell line. As shown in FIG. 4, none of the A or B fragments alone were able to rescue the glutamine synthetase deficient cell line, confirming that both the fragments are required for glutamine synthetase enzyme activity to be restored.

TABLE 6

Rescue dynamics of the GS fragments described in Table 4.

| Construct | Rescue of CHO-K1 GS KO | Days to >90% viability |
|---|---|---|
| WT | 4/4 | 14 |
| 1. | 2/4 | ~30 |
| 2. | 4/4 | 18 |
| 3. | 4/4 | ~24 |

TABLE 6-continued

Rescue dynamics of the GS fragments described in Table 4.

| Construct | Rescue of CHO-K1 GS KO | Days to >90% viability |
|---|---|---|
| 4. | 0/4 | No recovery |
| 5. | 4/4 | ~24 |

Figure 6:
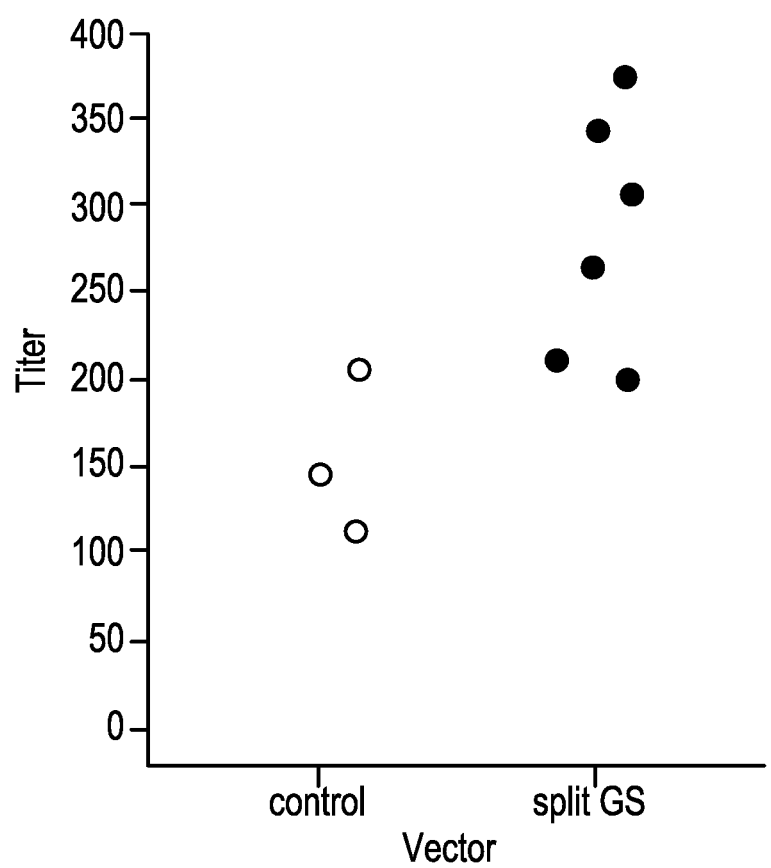
FIG. 6 is a graph showing the productivity of the cells from the construct 2 selected pools in a 10D fed-batch productivity assay and compared this to a control pool which was selected using a vector expressing a full length glutamine synthetase enzyme

These molecular complementation constructs were next tested in the context of expression vectors containing antibody light chain and heavy chain genes to assess their utility in a cell line development selection system. Two expression vectors were adapted to contain complementing glutamine synthetase fragments as shown in Table 4, one containing antibody light chain genes, and the second containing antibody heavy chain genes (FIG. 4). IRES sequences were also replaced with a version that is attenuated through mutation of an in frame ATG (BioTechniques 20:102-110 January 1996). This was to further reduce the levels of the glutamine synthetase fragments being expressed in comparison to the antibody genes and increase the selection stringency of the system in order to achieve a level of selective pressure that would be biased toward genome integration at highly transcriptionally active sites. The results from this study are shown in FIG. 6. Constructs 1, 2, 3 and 5 were tested in this assay and also linked the heavy chain and light chain genes in both orientations to each of the glutamine synthetase A and B fragments. Vectors containing the glutamine synthetase fragments from construct 2 were able to survive selection in glutamine free media.

The productivity of the cells from construct 2 selected pools was assessed in a 10D fed-batch productivity assay and compared to a control pool which was selected using a vector expressing a full length GS enzyme. As shown in FIG. 6, cells from construct 2 demonstrated high productivity

What is claimed is:

1. A vector comprising:
   a) a first nucleic acid encoding a first polypeptide, and
   b) a second nucleic acid encoding a second polypeptide, wherein the second polypeptide is an N-terminal mutant of glutamine synthetase (mutGS-NT), wherein the mutGS-NT comprises two or more mutations selected from the group consisting of W60A N61A D63A D63R S66A and D76A,
      wherein the transcription of the first nucleic acid is operably linked to transcription of the second nucleic acid,
   further comprising:
   c) a third nucleic acid encoding a third polypeptide wherein the third polypeptide is capable of associating with the first polypeptide to form a heteromeric complex, and
   d) a fourth nucleic acid which encodes fourth polypeptide, wherein the fourth polypeptide is a C-terminal mutant of glutamine synthetase (mutGS-CT), wherein the mutGS-CT comprises one or more mutations selected from the group consisting of E134A E136A E196A E203A N248A H253A N255A R319A and R324A,
      wherein the transcription of the third nucleic acid is operably linked to transcription of the fourth nucleic acid,
   wherein the glutamine synthetase has the amino acid sequence of SEQ ID NO: 1, the N-terminal mutant of glutamine synthetase and the C-terminal mutant of glutamine synthetase interact to provide a selectable activity, and further wherein the vector is capable of being transfected into mammalian cells and improving selection of transfected cells.

2. The vector of claim 1 wherein the heteromeric complex is an immunoglobulin.

3. The vector of claim 2 wherein the first nucleic acid encodes an immunoglobulin heavy chain, and the third nucleic acid encodes an immunoglobulin light chain.

4. The vector of claim 1, wherein an internal ribosomal entry site (IRES) occurs at a site selected from the group consisting of:
   a) a site between the first nucleic acid and the second nucleic acid;
   b) a site between the third nucleic acid and the fourth nucleic acid, and
   c) at sites between both first and second, and third and fourth nucleic acids.

5. The vector of claim 4, wherein the internal ribosomal entry site comprises SEQ ID NO:23.

6. The vector of claim 1, wherein the mutGS-NT is selected from the group consisting of W60A N61A D63A (mutGS-NT1; SEQ ID NO:6), W60A N61A D63A S66A (mutGS-NT2; SEQ ID NO:10) W60A N61A D63A S66A D76A (mutGS-NT3; SEQ ID NO:25), and W60A N61A D63R S66A (mutGS-NT4; SEQ ID NO:19); and the mutGS-CT is selected from the group consisting of E134A E136A E196A E203A (mutGS-CT1; SEQ ID NO:21) and N248A H253A N255A (mutGS-CT2; SEQ ID NO:22).

7. An isolated host cell that has been transfected, transformed or transduced with the vector of claim 1.

8. The host cell of claim 7, which is selected from the group consisting of CHO, VERO, BHK, HeLa, Cos, MDCK, 293, 3T3, a myeloma cell line, and WI38 cells.

9. A method of producing a heteromeric complex comprising the step of culturing the host cell of claim 8 under conditions wherein the heteromeric complex is expressed by the host cell.

10. The method of claim 9, wherein the heteromeric complex is an antibody.

11. The method of claim 10, further comprising isolating the heteromeric complex.

12. An expression system comprising:
   a) a first vector encoding a bicistronic transcript comprising a first nucleic acid encoding a first polypeptide that is operably linked to a second nucleic acid encoding a second polypeptide, wherein the second polypeptide is an N-terminal mutant of glutamine synthetase (mutGS-NT), wherein the mutGS-NT comprises two or more mutations selected from the group consisting of W60A N61A D63A D63R S66A and D76A, and
   b) a second vector encoding a bicistronic transcript comprising a third nucleic acid encoding a third polypeptide that is operably linked to a fourth nucleic acid encoding a fourth polypeptide, wherein the fourth polypeptide is a C-terminal mutant of glutamine synthetase (mutGS-CT), wherein the mutGS-CT comprises one or more mutations selected from the group consisting of E134A E136A E196A E203A N248A H253A N255A R319A and R324A, that is capable of associating with the N-terminal mutant of glutamine synthetase to provide a selectable activity, further wherein the third polypeptide is capable of associating with the first polypeptide to form a heteromeric complex;

and further wherein the glutamine synthetase has the amino acid sequence of SEQ ID NO: 1, and the expression system is capable of being transfected into mammalian cells and improving selection of said cells.

13. The expression system of claim 12, wherein the heteromeric complex is an immunoglobulin.

14. The expression system of claim 13, wherein the first nucleic acid encodes an immunoglobulin heavy chain, and the third nucleic acid encodes an immunoglobulin light chain.

15. The expression system of claim 12, wherein an internal ribosomal entry site (IRES) occurs at a site selected from the group consisting of:
   a) a site between the first nucleic acid and the second nucleic acid;
   b) a site between the third nucleic acid and the fourth nucleic acid, and
   c) at sites between both first and second, and third and fourth nucleic acids.

16. The expression system of claim 15, wherein the internal ribosomal entry site comprises SEQ ID NO:23.

17. The expression system of claim 12, wherein the mutGS-NT is selected from the group consisting of W60A N61A D63A (mutGS-NT1; SEQ ID NO:6), W60A N61A D63A S66A (mutGS-NT2; SEQ ID NO:10) W60A N61A D63A S66A D76A (mutGS-NT3; SEQ ID NO:25), and W60A N61A D63R S66A (mutGS-NT4; SEQ ID NO:19); and the mutGS-CT is selected from the group consisting of E134A E136A E196A E203A (mutGS-CT1; SEQ ID NO:21) and N248A H253A N255A (mutGS-CT2; SEQ ID NO:22).

18. An isolated host cell transfected, transformed or transduced with the expression system of claim 12.

19. The host cell of claim 18, which is selected from the group consisting of CHO, VERO, BHK, HeLa, Cos, MDCK, 293, 3T3, a myeloma cell line, and WI38 cells.

20. A method of producing a heteromeric complex comprising the step of culturing the host cell of claim 19 under conditions wherein the heteromeric complex is expressed by the host cell.

21. The method of claim 20, further comprising isolating the heteromeric complex.

* * * * *

SEQUENCE LISTING

```
<160> NUMBER OF SEQ ID NOS: 28

<210> SEQ ID NO 1
<211> LENGTH: 373
<212> TYPE: PRT
<213> ORGANISM: Mus musculus

<400> SEQUENCE: 1

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
```

```
            130                 135                 140
His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
        355                 360                 365

Phe Gln Tyr Lys Asn
    370

<210> SEQ ID NO 2
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 2

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Glu Leu Pro Glu Ala Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
```

```
            115                 120                 125
Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
                180                 185                 190

Thr Asn Ala Glu Val Met Pro Ala Gln Trp Glu Phe Gln Ile Gly Pro
                195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
                260                 265                 270

Ala Ile Asp Lys Leu Ser Lys Arg His Gln Tyr His Ile Arg Ala Tyr
                275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Lys Lys Gly Tyr
                325                 330                 335

Phe Glu Asp Arg Arg Pro Ser Ala Asn Cys Asp Pro Tyr Ala Val Thr
                340                 345                 350

Glu Ala Ile Val Arg Thr Cys Leu Leu Asn Glu Thr Gly Asp Glu Pro
                355                 360                 365

Phe Gln Tyr Lys Asn
    370

<210> SEQ ID NO 3
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 3

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
                20                  25                  30

Val Asp Gly Thr Gly Glu Gly Leu Arg Cys Lys Thr Arg Thr Leu Asp
                35                  40                  45

Cys Glu Pro Lys Cys Val Glu Glu Leu Pro Glu Trp Ala Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
```

```
                100                 105                 110
Leu Arg His Ile Cys Lys Arg Ile Met Asp Met Val Ser Asn Gln His
            115                 120                 125
Pro Trp Phe Gly Met Glu Gln Glu Tyr Thr Leu Met Gly Thr Asp Gly
        130                 135                 140
His Pro Phe Gly Trp Pro Ser Asn Gly Phe Pro Gly Pro Gln Gly Pro
145                 150                 155                 160
Tyr Tyr Cys Gly Val Gly Ala Asp Lys Ala Tyr Gly Arg Asp Ile Val
                165                 170                 175
Glu Ala His Tyr Arg Ala Cys Leu Tyr Ala Gly Val Lys Ile Thr Gly
            180                 185                 190
Thr Asn Ala Glu Val Met Pro Ala Gln Trp Glu Phe Gln Ile Gly Pro
        195                 200                 205
Cys Glu Gly Ile Arg Met Gly Asp His Leu Trp Ile Ala Arg Phe Ile
    210                 215                 220
Leu His Arg Val Cys Glu Asp Phe Gly Val Ile Ala Thr Phe Asp Pro
225                 230                 235                 240
Lys Pro Ile Pro Gly Asn Trp Asn Gly Ala Gly Cys His Thr Asn Phe
                245                 250                 255
Ser Thr Lys Ala Met Arg Glu Glu Asn Gly Leu Lys Cys Ile Glu Glu
            260                 265                 270
Ala Ile Asp Lys Leu Ser Lys Arg His Gln Tyr His Ile Arg Ala Tyr
        275                 280                 285
Asp Pro Lys Gly Gly Leu Asp Asn Ala Arg Arg Leu Thr Gly Phe His
    290                 295                 300
Glu Thr Ser Asn Ile Asn Asp Phe Ser Ala Gly Val Ala Asn Arg Gly
305                 310                 315                 320
Ala Ser Ile Arg Ile Pro Arg Thr Val Gly Gln Glu Lys Lys Gly Tyr
                325                 330                 335
Phe Glu Asp Arg Arg Pro Ser Ala Asn Cys Asp Pro Tyr Ala Val Thr
            340                 345                 350
Glu Ala Ile Val Arg Thr Cys Leu Leu Asn Glu Thr Gly Asp Glu Pro
        355                 360                 365
Phe Gln Tyr Lys Asn
    370
```

<210> SEQ ID NO 4
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 4

```
Met Ala Thr Ser Ala Ser Ser His Leu Asn Lys Gly Ile Lys Gln Met
1               5                   10                  15
Tyr Met Ser Leu Pro Gln Gly Glu Lys Val Gln Ala Met Tyr Ile Trp
                20                  25                  30
Val Asp Gly Thr Gly Glu Gly Leu Arg Cys Lys Thr Arg Thr Leu Asp
            35                  40                  45
Cys Glu Pro Lys Cys Val Glu Leu Pro Glu Trp Asn Phe Ala Gly
        50                  55                  60
Ser Ser Thr Phe Gln Ser Glu Gly Ser Asn Ser Asp Met Tyr Leu His
65                  70                  75                  80
Pro Val Ala Met Phe Arg Asp Pro Phe Arg Lys Asp Pro Asn Lys Leu
```

```
                85                  90                  95
Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
        355                 360                 365

Phe Gln Tyr Lys Asn
    370

<210> SEQ ID NO 5
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 5

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Glu Leu Pro Glu Trp Asn Phe Asp Gly
    50                  55                  60

Ser Ala Thr Phe Gln Ser Glu Gly Ser Asn Ser Asp Met Tyr Leu His
```

```
            65                  70                  75                  80
        Pro Val Ala Met Phe Arg Asp Pro Phe Arg Lys Asp Pro Asn Lys Leu
                        85                  90                  95

Val Leu Cys Glu Val Phe Lys Tyr Asn Arg Lys Pro Ala Glu Thr Asn
                        100                 105                 110

Leu Arg His Ile Cys Lys Arg Ile Met Asp Met Val Ser Asn Gln His
                        115                 120                 125

Pro Trp Phe Gly Met Glu Gln Glu Tyr Thr Leu Met Gly Thr Asp Gly
                        130                 135                 140

His Pro Phe Gly Trp Pro Ser Asn Gly Phe Pro Gly Pro Gln Gly Pro
        145                 150                 155                 160

Tyr Tyr Cys Gly Val Gly Ala Asp Lys Ala Tyr Gly Arg Asp Ile Val
                        165                 170                 175

Glu Ala His Tyr Arg Ala Cys Leu Tyr Ala Gly Val Lys Ile Thr Gly
                        180                 185                 190

Thr Asn Ala Glu Val Met Pro Ala Gln Trp Glu Phe Gln Ile Gly Pro
                        195                 200                 205

Cys Glu Gly Ile Arg Met Gly Asp His Leu Trp Ile Ala Arg Phe Ile
                        210                 215                 220

Leu His Arg Val Cys Glu Asp Phe Gly Val Ile Ala Thr Phe Asp Pro
        225                 230                 235                 240

Lys Pro Ile Pro Gly Asn Trp Asn Gly Ala Gly Cys His Thr Asn Phe
                        245                 250                 255

Ser Thr Lys Ala Met Arg Glu Glu Asn Gly Leu Lys Cys Ile Glu Glu
                        260                 265                 270

Ala Ile Asp Lys Leu Ser Lys Arg His Gln Tyr His Ile Arg Ala Tyr
                        275                 280                 285

Asp Pro Lys Gly Gly Leu Asp Asn Ala Arg Arg Leu Thr Gly Phe His
                        290                 295                 300

Glu Thr Ser Asn Ile Asn Asp Phe Ser Ala Gly Val Ala Asn Arg Gly
        305                 310                 315                 320

Ala Ser Ile Arg Ile Pro Arg Thr Val Gly Gln Glu Lys Lys Gly Tyr
                        325                 330                 335

Phe Glu Asp Arg Arg Pro Ser Ala Asn Cys Asp Pro Tyr Ala Val Thr
                        340                 345                 350

Glu Ala Ile Val Arg Thr Cys Leu Leu Asn Glu Thr Gly Asp Glu Pro
                        355                 360                 365

Phe Gln Tyr Lys Asn
                        370

<210> SEQ ID NO 6
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 6

Met Ala Thr Ser Ala Ser Ser His Leu Asn Lys Gly Ile Lys Gln Met
        1               5                   10                  15

Tyr Met Ser Leu Pro Gln Gly Glu Lys Val Gln Ala Met Tyr Ile Trp
                        20                  25                  30

Val Asp Gly Thr Gly Glu Gly Leu Arg Cys Lys Thr Arg Thr Leu Asp
                        35                  40                  45

Cys Glu Pro Lys Cys Val Glu Glu Leu Pro Glu Ala Ala Phe Ala Gly
```

```
            50                  55                  60
Ser Ser Thr Phe Gln Ser Glu Gly Ser Asn Ser Asp Met Tyr Leu His
 65                  70                  75                  80

Pro Val Ala Met Phe Arg Asp Pro Phe Arg Lys Asp Pro Asn Lys Leu
                 85                  90                  95

Val Leu Cys Glu Val Phe Lys Tyr Asn Arg Lys Pro Ala Glu Thr Asn
                100                 105                 110

Leu Arg His Ile Cys Lys Arg Ile Met Asp Met Val Ser Asn Gln His
            115                 120                 125

Pro Trp Phe Gly Met Glu Gln Glu Tyr Thr Leu Met Gly Thr Asp Gly
            130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
            195                 200                 205

Cys Glu Gly Ile Arg Met Gly Asp His Leu Trp Ile Ala Arg Phe Ile
210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
            275                 280                 285

Asp Pro Lys Gly Gly Leu Asp Asn Ala Arg Arg Leu Thr Gly Phe His
            290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
            355                 360                 365

Phe Gln Tyr Lys Asn
            370

<210> SEQ ID NO 7
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 7

Met Ala Thr Ser Ala Ser Ser His Leu Asn Lys Gly Ile Lys Gln Met
  1               5                  10                  15

Tyr Met Ser Leu Pro Gln Gly Glu Lys Val Gln Ala Met Tyr Ile Trp
                 20                  25                  30

Val Asp Gly Thr Gly Glu Gly Leu Arg Cys Lys Thr Arg Thr Leu Asp
```

```
            35                  40                  45
Cys Glu Pro Lys Cys Val Glu Glu Leu Pro Glu Ala Ala Phe Asp Gly
 50                  55                  60

Ser Ala Thr Phe Gln Ser Glu Gly Ser Asn Ser Asp Met Tyr Leu His
 65                  70                  75                  80

Pro Val Ala Met Phe Arg Asp Pro Phe Arg Lys Asp Pro Asn Lys Leu
                 85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
            115                 120                 125

Pro Trp Phe Gly Met Glu Gln Glu Tyr Thr Leu Met Gly Thr Asp Gly
130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
            195                 200                 205

Cys Glu Gly Ile Arg Met Gly Asp His Leu Trp Ile Ala Arg Phe Ile
210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
            275                 280                 285

Asp Pro Lys Gly Gly Leu Asp Asn Ala Arg Arg Leu Thr Gly Phe His
290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
            355                 360                 365

Phe Gln Tyr Lys Asn
    370

<210> SEQ ID NO 8
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 8

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
```

```
            20                  25                  30
Val Asp Gly Thr Gly Glu Gly Leu Arg Cys Lys Thr Arg Thr Leu Asp
            35                  40                  45
Cys Glu Pro Lys Cys Val Glu Leu Pro Glu Ala Asn Phe Ala Gly
    50                  55                  60
Ser Ala Thr Phe Gln Ser Glu Gly Ser Asn Ser Asp Met Tyr Leu His
65                  70                  75                  80
Pro Val Ala Met Phe Arg Asp Pro Phe Arg Lys Asp Pro Asn Lys Leu
                85                  90                  95
Val Leu Cys Glu Val Phe Lys Tyr Asn Arg Lys Pro Ala Glu Thr Asn
            100                 105                 110
Leu Arg His Ile Cys Lys Arg Ile Met Asp Met Val Ser Asn Gln His
            115                 120                 125
Pro Trp Phe Gly Met Glu Gln Glu Tyr Thr Leu Met Gly Thr Asp Gly
            130                 135                 140
His Pro Phe Gly Trp Pro Ser Asn Gly Phe Pro Gly Pro Gln Gly Pro
145                 150                 155                 160
Tyr Tyr Cys Gly Val Gly Ala Asp Lys Ala Tyr Gly Arg Asp Ile Val
                165                 170                 175
Glu Ala His Tyr Arg Ala Cys Leu Tyr Ala Gly Val Lys Ile Thr Gly
                180                 185                 190
Thr Asn Ala Glu Val Met Pro Ala Gln Trp Glu Phe Gln Ile Gly Pro
            195                 200                 205
Cys Glu Gly Ile Arg Met Gly Asp His Leu Trp Ile Ala Arg Phe Ile
            210                 215                 220
Leu His Arg Val Cys Glu Asp Phe Gly Val Ile Ala Thr Phe Asp Pro
225                 230                 235                 240
Lys Pro Ile Pro Gly Asn Trp Asn Gly Ala Gly Cys His Thr Asn Phe
                245                 250                 255
Ser Thr Lys Ala Met Arg Glu Glu Asn Gly Leu Lys Cys Ile Glu Glu
                260                 265                 270
Ala Ile Asp Lys Leu Ser Lys Arg His Gln Tyr His Ile Arg Ala Tyr
            275                 280                 285
Asp Pro Lys Gly Gly Leu Asp Asn Ala Arg Arg Leu Thr Gly Phe His
            290                 295                 300
Glu Thr Ser Asn Ile Asn Asp Phe Ser Ala Gly Val Ala Asn Arg Gly
305                 310                 315                 320
Ala Ser Ile Arg Ile Pro Arg Thr Val Gly Gln Glu Lys Lys Gly Tyr
                325                 330                 335
Phe Glu Asp Arg Arg Pro Ser Ala Asn Cys Asp Pro Tyr Ala Val Thr
            340                 345                 350
Glu Ala Ile Val Arg Thr Cys Leu Leu Asn Glu Thr Gly Asp Glu Pro
            355                 360                 365
Phe Gln Tyr Lys Asn
    370

<210> SEQ ID NO 9
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 9

Met Ala Thr Ser Ala Ser Ser His Leu Asn Lys Gly Ile Lys Gln Met
```

```
              1               5                  10                 15
          Tyr Met Ser Leu Pro Gln Gly Glu Lys Val Gln Ala Met Tyr Ile Trp
                          20                  25                  30

Val Asp Gly Thr Gly Glu Gly Leu Arg Cys Lys Thr Arg Thr Leu Asp
                          35                  40                  45

Cys Glu Pro Lys Cys Val Glu Leu Pro Glu Trp Ala Phe Ala Gly
                          50                  55                  60

Ser Ala Thr Phe Gln Ser Glu Gly Ser Asn Ser Asp Met Tyr Leu His
           65                  70                  75                  80

Pro Val Ala Met Phe Arg Asp Pro Phe Arg Lys Asp Pro Asn Lys Leu
                              85                  90                  95

Val Leu Cys Glu Val Phe Lys Tyr Asn Arg Lys Pro Ala Glu Thr Asn
                          100                 105                 110

Leu Arg His Ile Cys Lys Arg Ile Met Asp Met Val Ser Asn Gln His
                          115                 120                 125

Pro Trp Phe Gly Met Glu Gln Glu Tyr Thr Leu Met Gly Thr Asp Gly
                          130                 135                 140

His Pro Phe Gly Trp Pro Ser Asn Gly Phe Pro Gly Pro Gln Gly Pro
          145                 150                 155                 160

Tyr Tyr Cys Gly Val Gly Ala Asp Lys Ala Tyr Gly Arg Asp Ile Val
                          165                 170                 175

Glu Ala His Tyr Arg Ala Cys Leu Tyr Ala Gly Val Lys Ile Thr Gly
                          180                 185                 190

Thr Asn Ala Glu Val Met Pro Ala Gln Trp Glu Phe Gln Ile Gly Pro
                          195                 200                 205

Cys Glu Gly Ile Arg Met Gly Asp His Leu Trp Ile Ala Arg Phe Ile
                          210                 215                 220

Leu His Arg Val Cys Glu Asp Phe Gly Val Ile Ala Thr Phe Asp Pro
          225                 230                 235                 240

Lys Pro Ile Pro Gly Asn Trp Asn Gly Ala Gly Cys His Thr Asn Phe
                              245                 250                 255

Ser Thr Lys Ala Met Arg Glu Glu Asn Gly Leu Lys Cys Ile Glu Glu
                          260                 265                 270

Ala Ile Asp Lys Leu Ser Lys Arg His Gln Tyr His Ile Arg Ala Tyr
                          275                 280                 285

Asp Pro Lys Gly Gly Leu Asp Asn Ala Arg Arg Leu Thr Gly Phe His
                          290                 295                 300

Glu Thr Ser Asn Ile Asn Asp Phe Ser Ala Gly Val Ala Asn Arg Gly
          305                 310                 315                 320

Ala Ser Ile Arg Ile Pro Arg Thr Val Gly Gln Glu Lys Lys Gly Tyr
                          325                 330                 335

Phe Glu Asp Arg Arg Pro Ser Ala Asn Cys Asp Pro Tyr Ala Val Thr
                          340                 345                 350

Glu Ala Ile Val Arg Thr Cys Leu Leu Asn Glu Thr Gly Asp Glu Pro
                          355                 360                 365

Phe Gln Tyr Lys Asn
              370

<210> SEQ ID NO 10
<211> LENGTH: 373
<212> TYPE: PRT
<213> ORGANISM: Artificial Sequence
<220> FEATURE:
<223> OTHER INFORMATION: Synthetic Polypeptide
```

```
<400> SEQUENCE: 10

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Glu Leu Pro Ala Ala Phe Ala Gly
    50                  55                  60

Ser Ala Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
        355                 360                 365

Phe Gln Tyr Lys Asn
    370

<210> SEQ ID NO 11
<211> LENGTH: 373
<212> TYPE: PRT
<213> ORGANISM: Artificial Sequence
```

<220> FEATURE:
<223> OTHER INFORMATION: Synthetic Polypeptide

<400> SEQUENCE: 11

```
Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Ala Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
        355                 360                 365

Phe Gln Tyr Lys Asn
    370
```

<210> SEQ ID NO 12

<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 12

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Ala Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
        355                 360                 365

Phe Gln Tyr Lys Asn
    370

<210> SEQ ID NO 13
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 13

```
Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Ala Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
        355                 360                 365
```

Phe Gln Tyr Lys Asn
    370

<210> SEQ ID NO 14
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 14

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Ala Phe Gln Ile Gly Pro
        195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

-continued

Glu Ala Ile Val Arg Thr Cys Leu Leu Asn Glu Thr Gly Asp Glu Pro
            355                 360                 365

Phe Gln Tyr Lys Asn
    370

<210> SEQ ID NO 15
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 15

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Ala Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

```
Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
        355                 360                 365

Phe Gln Tyr Lys Asn
    370

<210> SEQ ID NO 16
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 16

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys Ala Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320
```

-continued

```
Ala Ser Ile Arg Ile Pro Arg Thr Val Gly Gln Lys Lys Gly Tyr
            325                 330                 335

Phe Glu Asp Arg Arg Pro Ser Ala Asn Cys Asp Pro Tyr Ala Val Thr
                340                 345                 350

Glu Ala Ile Val Arg Thr Cys Leu Leu Asn Glu Thr Gly Asp Glu Pro
            355                 360                 365

Phe Gln Tyr Lys Asn
    370

<210> SEQ ID NO 17
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 17

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
                20                  25                  30

Val Asp Gly Thr Gly Glu Gly Leu Arg Cys Lys Thr Arg Thr Leu Asp
            35                  40                  45

Cys Glu Pro Lys Cys Val Glu Glu Leu Pro Glu Trp Asn Phe Asp Gly
        50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Ala Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300
```

```
Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
        355                 360                 365

Phe Gln Tyr Lys Asn
    370
```

<210> SEQ ID NO 18
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 18

```
Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
                20                  25                  30

Val Asp Gly Thr Gly Glu Gly Leu Arg Cys Lys Thr Arg Thr Leu Asp
            35                  40                  45

Cys Glu Pro Lys Cys Val Glu Glu Leu Pro Glu Trp Asn Phe Asp Gly
        50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
        275                 280                 285
```

Asp Pro Lys Gly Gly Leu Asp Asn Ala Arg Arg Leu Thr Gly Phe His
          290                 295                 300

Glu Thr Ser Asn Ile Asn Asp Phe Ser Ala Gly Val Ala Asn Ala Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
        355                 360                 365

Phe Gln Tyr Lys Asn
    370

<210> SEQ ID NO 19
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 19

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Leu Pro Glu Ala Ala Phe Arg Gly
    50                  55                  60

Ser Ala Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

```
Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
        290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
                340                 345                 350

Glu Ala Ile Val Arg Thr Cys Leu Leu Asn Glu Thr Gly Asp Glu Pro
                355                 360                 365

Phe Gln Tyr Lys Asn
        370
```

<210> SEQ ID NO 20
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 20

```
Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
                100                 105                 110

Leu Arg His Ile Cys Lys Arg Ile Met Asp Met Val Ser Asn Gln His
            115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
                180                 185                 190

Thr Asn Ala Glu Val Met Pro Ala Gln Trp Glu Phe Gln Ile Gly Pro
            195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255
```

```
Ser Thr Lys Ala Met Arg Glu Glu Asn Gly Leu Lys Cys Ile Glu Glu
        260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
        290                 295                 300

Glu Thr Ser Asn Ile Asn Asp Phe Ser Ala Gly Val Ala Asn Arg Gly
305                 310                 315                 320

Ala Ser Ile Ala Ile Pro Arg Thr Val Gly Gln Lys Lys Gly Tyr
                    325                 330                 335

Phe Glu Asp Arg Arg Pro Ser Ala Asn Cys Asp Pro Tyr Ala Val Thr
                    340                 345                 350

Glu Ala Ile Val Arg Thr Cys Leu Leu Asn Glu Thr Gly Asp Glu Pro
        355                 360                 365

Phe Gln Tyr Lys Asn
        370

<210> SEQ ID NO 21
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 21

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
                20                  25                  30

Val Asp Gly Thr Gly Glu Gly Leu Arg Cys Lys Thr Arg Thr Leu Asp
            35                  40                  45

Cys Glu Pro Lys Cys Val Glu Glu Leu Pro Glu Trp Asn Phe Asp Gly
        50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Ala Gln Ala Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Ala Val Met Pro Ala Gln Trp Ala Phe Gln Ile Gly Pro
        195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240
```

```
Lys Pro Ile Pro Gly Asn Trp Asn Gly Ala Gly Cys His Thr Asn Phe
            245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
            275                 280                 285

Asp Pro Lys Gly Gly Leu Asp Asn Ala Arg Arg Leu Thr Gly Phe His
            290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
            325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
            355                 360                 365

Phe Gln Tyr Lys Asn
            370

<210> SEQ ID NO 22
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 22

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
            35                  40                  45

Cys Glu Pro Lys Cys Val Glu Glu Leu Pro Glu Trp Asn Phe Asp Gly
        50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
            85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
            115                 120                 125

Pro Trp Phe Gly Met Glu Gln Glu Tyr Thr Leu Met Gly Thr Asp Gly
            130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
            165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
            195                 200                 205

Cys Glu Gly Ile Arg Met Gly Asp His Leu Trp Ile Ala Arg Phe Ile
            210                 215                 220
```

```
Leu His Arg Val Cys Glu Asp Phe Gly Val Ile Ala Thr Phe Asp Pro
225                 230                 235                 240

Lys Pro Ile Pro Gly Asn Trp Ala Gly Ala Gly Cys Ala Thr Ala Phe
            245                 250                 255

Ser Thr Lys Ala Met Arg Glu Glu Asn Gly Leu Lys Cys Ile Glu Glu
        260                 265                 270

Ala Ile Asp Lys Leu Ser Lys Arg His Gln Tyr His Ile Arg Ala Tyr
    275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
        355                 360                 365

Phe Gln Tyr Lys Asn
    370

<210> SEQ ID NO 23
<211> LENGTH: 33
<212> TYPE: PRT
<213> ORGANISM: Encephalomyocarditis virus

<400> SEQUENCE: 23

Gly Ala Thr Gly Ala Thr Ala Ala Thr Ala Cys Cys Cys Thr Cys Gly
1               5                   10                  15

Ala Gly Ala Thr Cys Cys Gly Thr Gly Cys Cys Ala Thr Cys Ala Thr
            20                  25                  30

Gly

<210> SEQ ID NO 24
<211> LENGTH: 24
<212> TYPE: PRT
<213> ORGANISM: Encephalomyocarditis virus

<400> SEQUENCE: 24

Gly Ala Thr Gly Ala Thr Ala Ala Thr Ala Thr Gly Gly Cys Cys Ala
1               5                   10                  15

Cys Ala Ala Cys Cys Ala Thr Gly
            20

<210> SEQ ID NO 25
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 25

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45
```

Cys Glu Pro Lys Cys Val Glu Leu Pro Glu Ala Ala Phe Ala Gly
            50                  55                  60

Ser Ala Thr Phe Gln Ser Glu Gly Ser Asn Ser Ala Met Tyr Leu His
 65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
        355                 360                 365

Phe Gln Tyr Lys Asn
    370

<210> SEQ ID NO 26
<211> LENGTH: 47
<212> TYPE: PRT
<213> ORGANISM: Saccharomyces cerevisiae

<400> SEQUENCE: 26

Met Ser Asp Arg Met Lys Gln Leu Glu Asp Lys Val Glu Glu Leu Leu
 1               5                  10                  15

Ser Lys Val Tyr His Leu Glu Asn Glu Val Ala Arg Leu Lys Lys Leu
            20                  25                  30

Val Gly Glu Arg Gly Gly Gly Gly Ser Gly Gly Gly Gly Gly Ser

```
                35                  40                  45

<210> SEQ ID NO 27
<211> LENGTH: 46
<212> TYPE: PRT
<213> ORGANISM: Saccharomyces cerevisiae

<400> SEQUENCE: 27

Gly Gly Gly Gly Ser Gly Gly Gly Gly Ser Ser Asp Arg Met Lys
1               5                   10                  15

Gln Leu Glu Asp Lys Val Glu Leu Leu Ser Lys Val Tyr His Leu
                20                  25                  30

Glu Asn Glu Val Ala Arg Leu Lys Lys Leu Val Gly Glu Arg
                35                  40                  45

<210> SEQ ID NO 28
<211> LENGTH: 373
<212> TYPE: PRT
<213> ORGANISM: Mus musculus

<400> SEQUENCE: 28

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
                20                  25                  30

Val Asp Gly Thr Gly Glu Gly Leu Arg Cys Lys Thr Arg Thr Leu Asp
                35                  40                  45

Cys Glu Pro Lys Cys Val Glu Glu Leu Pro Glu Trp Asn Phe Asp Gly
                50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
                100                 105                 110

Leu Arg His Ile Cys Lys Arg Ile Met Asp Met Val Ser Asn Gln His
                115                 120                 125

Pro Trp Phe Gly Met Glu Gln Glu Tyr Thr Leu Met Gly Thr Asp Gly
                130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
                180                 185                 190

Thr Asn Ala Glu Val Met Pro Ala Gln Trp Glu Phe Gln Ile Gly Pro
                195                 200                 205

Cys Glu Gly Ile Arg Met Gly Asp His Leu Trp Ile Ala Arg Phe Ile
                210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
                260                 265                 270

Ala Ile Asp Lys Leu Ser Lys Arg His Gln Tyr His Ile Arg Ala Tyr
```

-continued

```
                275                 280                 285
Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
            355                 360                 365

Phe Gln Tyr Lys Asn
    370
```